(12) United States Patent
Keuleers et al.

(10) Patent No.: US 10,899,518 B2
(45) Date of Patent: Jan. 26, 2021

(54) WATER-SOLUBLE PACKETS

(71) Applicant: MONOSOL, LLC, Merrillville, IN (US)

(72) Inventors: Robby Renilde Francois Keuleers, Lippelo (BE); Steven G. Friedrich, Crown Point, IN (US); Lee K. Yeung, Highland, IN (US); Shinsuke Nii, Merrillville, IN (US)

(73) Assignee: MONOSOL, LLC, Merrillville, IN (US)

( * ) Notice: Subject to any disclaimer, the term of this patent is extended or adjusted under 35 U.S.C. 154(b) by 553 days.

(21) Appl. No.: 15/620,366

(22) Filed: Jun. 12, 2017

(65) Prior Publication Data
US 2018/0002084 A1    Jan. 4, 2018

Related U.S. Application Data

(60) Provisional application No. 62/349,440, filed on Jun. 13, 2016.

(51) Int. Cl.
*B65D 65/46* (2006.01)
*B32B 1/02* (2006.01)
(Continued)

(52) U.S. Cl.
CPC .......... *B65D 65/46* (2013.01); *B29C 66/7316* (2013.01); *B32B 1/02* (2013.01);
(Continued)

(58) Field of Classification Search
CPC .. B32B 1/02; B32B 1/08; B65D 75/04; B65D 75/06; B65D 75/08; B65D 75/12;
(Continued)

(56) References Cited

U.S. PATENT DOCUMENTS

| 1,029,446 A | 6/1912 | Hunt |
| 3,580,390 A | 5/1971 | Shull, Jr. |

(Continued)

FOREIGN PATENT DOCUMENTS

| CA | 2913731 A1 | 12/2014 |
| CN | 105377965 A | 3/2016 |

(Continued)

OTHER PUBLICATIONS

Gordon et al., The Chemist's Companion, pp. 30-36, John Wiley & Sons Publishing (1972).

(Continued)

*Primary Examiner* — Walter Aughenbaugh
(74) *Attorney, Agent, or Firm* — Marshall, Gerstein & Borun LLP

(57) ABSTRACT

The disclosure provides a water soluble pouch including at least two sealed compartments, the pouch including outer walls including water soluble film including a water soluble resin, and an inner wall including water soluble film including a water soluble resin, the outer wall films being sealed to the inner wall film, the outer wall films being characterized by: a dissolution time of 300 seconds or less, the water soluble resin of the outer wall films having a viscosity in a range of 14.5 cP to 25 cP, and a pouch strength of at least 200 N, and the inner wall film being characterized by: a dissolution time of 300 seconds or less, the water soluble resin of the inner film having viscosity in a range of 12 cP to 14.5 cP, and a tackiness value of at least 1500 g/s.

22 Claims, 2 Drawing Sheets

(51) Int. Cl.

| | | |
|---|---|---|
| *B65D 85/80* | (2006.01) | |
| *B65D 75/04* | (2006.01) | |
| *B65D 75/06* | (2006.01) | |
| *B65D 75/22* | (2006.01) | |
| *B65D 75/30* | (2006.01) | |
| *B65D 75/20* | (2006.01) | |
| *B65D 75/08* | (2006.01) | |
| *B65D 75/12* | (2006.01) | |
| *B65D 75/32* | (2006.01) | |
| *B32B 1/08* | (2006.01) | |
| *B65D 85/808* | (2006.01) | |
| *B65B 9/04* | (2006.01) | |
| *B65B 47/02* | (2006.01) | |
| *B65B 47/10* | (2006.01) | |
| *B65B 51/10* | (2006.01) | |
| *C11D 17/04* | (2006.01) | |
| *B29C 65/00* | (2006.01) | |
| *B65D 53/06* | (2006.01) | |
| *C07C 31/20* | (2006.01) | |
| *C07C 57/145* | (2006.01) | |
| *C08J 5/12* | (2006.01) | |
| *C08L 29/04* | (2006.01) | |

(52) U.S. Cl.
CPC ............... *B32B 1/08* (2013.01); *B65B 9/042* (2013.01); *B65B 47/02* (2013.01); *B65B 47/10* (2013.01); *B65B 51/10* (2013.01); *B65D 53/06* (2013.01); *B65D 75/04* (2013.01); *B65D 75/06* (2013.01); *B65D 75/08* (2013.01); *B65D 75/12* (2013.01); *B65D 75/20* (2013.01); *B65D 75/22* (2013.01); *B65D 75/30* (2013.01); *B65D 75/322* (2013.01); *B65D 85/808* (2013.01); *C07C 31/202* (2013.01); *C07C 57/145* (2013.01); *C08J 5/121* (2013.01); *C08L 29/04* (2013.01); *C11D 17/043* (2013.01); *C11D 17/044* (2013.01); *C11D 17/045* (2013.01)

(58) Field of Classification Search
CPC ......... B65D 75/20; B65D 75/22; B65D 75/30; B65D 72/322; B65D 65/46; B65D 85/808
See application file for complete search history.

(56) References Cited

U.S. PATENT DOCUMENTS

| | | | |
|---|---|---|---|
| 3,892,905 | A | 7/1975 | Albert |
| RE29,059 | E | 12/1976 | Kack et al. |
| 4,119,604 | A | 10/1978 | Wysong |
| 4,155,971 | A | 5/1979 | Wysong |
| 4,156,047 | A | 5/1979 | Wysong |
| 4,466,431 | A | 8/1984 | Tharrat et al. |
| 4,626,372 | A | 12/1986 | Kaufmann et al. |
| 4,681,228 | A | 7/1987 | Kerry et al. |
| 4,692,494 | A | 9/1987 | Sonenstein |
| 4,747,976 | A | 5/1988 | Yang et al. |
| 5,135,982 | A | 8/1992 | Matsumoto et al. |
| 5,316,688 | A | 5/1994 | Gladfelter et al. |
| 5,362,532 | A | 11/1994 | Famili et al. |
| 5,558,228 | A | 9/1996 | Jackisch et al. |
| 5,674,578 | A | 10/1997 | Giori |
| 5,691,015 | A | 11/1997 | Tsukamoto et al. |
| 6,204,223 | B1 | 3/2001 | Holmes et al. |
| 6,787,512 | B1 | 9/2004 | Verrall et al. |
| 6,960,627 | B2 | 11/2005 | Huth et al. |
| 7,022,656 | B2 | 4/2006 | Verrall et al. |
| 7,476,325 | B2 | 1/2009 | Tufano et al. |
| 7,547,737 | B2 | 6/2009 | Kochvar et al. |
| 7,642,226 | B2 | 1/2010 | Verrall et al. |
| 7,749,952 | B2 | 7/2010 | Zhang et al. |
| 7,754,318 | B2 | 7/2010 | Kitamura et al. |
| 7,786,027 | B2 | 8/2010 | Aouad et al. |
| 7,867,968 | B1 | 1/2011 | Aouad |
| 7,871,976 | B1 | 1/2011 | Aouad |
| 8,163,104 | B2 | 4/2012 | Swidersky et al. |
| 8,276,756 | B2 | 10/2012 | Denome et al. |
| 8,333,033 | B2 | 12/2012 | Bell |
| 8,697,624 | B2 | 4/2014 | Denome et al. |
| 8,728,593 | B2 | 5/2014 | Vicari et al. |
| 8,754,025 | B2 | 6/2014 | Wiedemann et al. |
| 8,835,372 | B2 | 9/2014 | Jennewein |
| 8,905,236 | B2 | 12/2014 | Denome et al. |
| 8,980,817 | B2 | 3/2015 | Wiedemann et al. |
| 9,133,329 | B2 | 9/2015 | Denome et al. |
| 9,267,098 | B2 | 2/2016 | Miracle |
| 9,404,071 | B2 | 8/2016 | Labeque et al. |
| 10,183,794 | B2 | 1/2019 | Souter et al. |
| 10,240,114 | B2 | 3/2019 | Labeque et al. |
| 10,336,973 | B2 | 7/2019 | Labeque et al. |
| 10,370,627 | B2 | 8/2019 | Courchay et al. |
| 10,377,980 | B2 | 8/2019 | Souter et al. |
| 10,619,042 | B2 | 4/2020 | Labeque et al. |
| 10,745,655 | B2 | 8/2020 | Courchay et al. |
| 2004/0072709 | A1 | 4/2004 | Wiedemann et al. |
| 2004/0092635 | A1 | 5/2004 | Kitamura et al. |
| 2004/0144682 | A1 | 7/2004 | Altmayer |
| 2006/0172910 | A1 | 8/2006 | Brooker et al. |
| 2006/0173430 | A1 | 8/2006 | Lee et al. |
| 2007/0003719 | A1 | 1/2007 | Balchin |
| 2008/0097029 | A1 | 4/2008 | Yang |
| 2008/0110370 | A1 | 5/2008 | Verrall et al. |
| 2008/0146481 | A1 | 6/2008 | Brown et al. |
| 2008/0185347 | A1 | 8/2008 | Tufano et al. |
| 2009/0215664 | A1 | 8/2009 | Raehse |
| 2009/0291282 | A1 | 11/2009 | Kitamura et al. |
| 2009/0312220 | A1 | 12/2009 | Boutoille et al. |
| 2010/0113318 | A1 | 5/2010 | Wiedemann et al. |
| 2010/0180549 | A1 | 7/2010 | Ayats et al. |
| 2011/0054111 | A1 | 3/2011 | McLachlan et al. |
| 2011/0062308 | A1 | 3/2011 | Hammond et al. |
| 2011/0152163 | A1 | 6/2011 | Labeque et al. |
| 2011/0186467 | A1 | 8/2011 | Denome et al. |
| 2011/0188784 | A1 | 8/2011 | Denome et al. |
| 2011/0189413 | A1 | 8/2011 | Denome et al. |
| 2012/0294969 | A1 | 11/2012 | Koch et al. |
| 2013/0240388 | A1 | 9/2013 | Koch et al. |
| 2014/0110301 | A1 | 4/2014 | Carrier et al. |
| 2014/0124454 | A1 | 5/2014 | Nichols et al. |
| 2014/0162929 | A1 | 6/2014 | Labeque et al. |
| 2014/0345064 | A1 | 11/2014 | Koch et al. |
| 2014/0356603 | A1 | 12/2014 | Kumar et al. |
| 2014/0371411 | A1 | 12/2014 | DiPietro et al. |
| 2015/0080561 | A1 | 3/2015 | Torres et al. |
| 2015/0093526 | A1 | 4/2015 | Denome et al. |
| 2015/0158646 | A1 | 6/2015 | Meier et al. |
| 2015/0184116 | A1 | 7/2015 | Wiedemann et al. |
| 2015/0275152 | A1 | 10/2015 | Brooker et al. |
| 2015/0336692 | A1 | 11/2015 | Brandt Sanz et al. |
| 2016/0024446 | A1 | 1/2016 | Lee et al. |
| 2016/0102278 | A1 | 4/2016 | Labeque et al. |
| 2016/0102279 | A1 | 4/2016 | Labeque et al. |
| 2016/0172910 | A1 | 6/2016 | Saito et al. |
| 2016/0200501 | A1 | 7/2016 | Lee et al. |
| 2016/0251148 | A1 | 9/2016 | Edwards |
| 2016/0326285 | A1 | 11/2016 | Mori et al. |
| 2017/0218146 | A1 | 8/2017 | Childers et al. |
| 2017/0226298 | A1 | 8/2017 | Friedrich et al. |
| 2017/0226338 | A1 | 8/2017 | Friedrich et al. |
| 2017/0233539 | A1 | 8/2017 | Friedrich et al. |
| 2017/0259976 | A1 | 9/2017 | Lee et al. |
| 2017/0275394 | A1 | 9/2017 | Mori et al. |
| 2017/0298216 | A1 | 10/2017 | Labeque et al. |
| 2017/0298308 | A1 | 10/2017 | Labeque et al. |
| 2017/0355934 | A1 | 12/2017 | Courchay et al. |
| 2017/0355935 | A1 | 12/2017 | Courchay et al. |
| 2017/0355936 | A1 | 12/2017 | Souter et al. |
| 2017/0355937 | A1 | 12/2017 | Courchay et al. |
| 2017/0355938 | A1 | 12/2017 | Lee et al. |
| 2017/0369217 | A1 | 12/2017 | Souter et al. |

(56) References Cited

U.S. PATENT DOCUMENTS

| | | | |
|---|---|---|---|
| 2017/0369822 A1 | 12/2017 | Souter et al. |
| 2017/0369823 A1 | 12/2017 | Souter et al. |
| 2018/0002647 A1 | 1/2018 | Souter et al. |
| 2018/0127200 A1 | 5/2018 | Edwards |
| 2020/0048587 A1 | 2/2020 | Courchay et al. |
| 2020/0199344 A1 | 6/2020 | Labeque et al. |

FOREIGN PATENT DOCUMENTS

| | | |
|---|---|---|
| CN | 105601974 A | 5/2016 |
| EP | 0291198 A2 | 11/1988 |
| EP | 0407301 A1 | 1/1991 |
| EP | 0989803 A1 | 4/2000 |
| EP | 01298196 A1 | 4/2003 |
| EP | 1432614 A1 | 6/2004 |
| EP | 1466938 A1 | 10/2004 |
| EP | 1512701 | 3/2005 |
| EP | 2021172 B1 | 5/2010 |
| EP | 2258820 A1 | 12/2010 |
| EP | 2049587 B1 | 3/2013 |
| EP | 3025848 A1 | 6/2016 |
| EP | 3138896 A1 | 3/2017 |
| EP | 3202880 A1 | 8/2017 |
| EP | 3207083 A1 | 8/2017 |
| EP | 3207085 A2 | 8/2017 |
| JP | S52015576 A | 2/1977 |
| JP | H0370760 B2 | 11/1991 |
| JP | H04164998 A | 6/1992 |
| JP | H06298273 A | 10/1994 |
| JP | H06298274 A | 10/1994 |
| JP | H06340899 A | 12/1994 |
| JP | H08229112 A | 9/1996 |
| JP | H09040834 A | 2/1997 |
| JP | H09272773 A | 10/1997 |
| JP | 2000169896 A | 6/2000 |
| JP | 2001247625 A | 9/2001 |
| JP | 2002003896 A | 1/2002 |
| JP | 2002003897 A | 1/2002 |
| JP | 2005-089655 A | 4/2005 |
| JP | 2006063242 A | 3/2006 |
| JP | 4095595 B2 | 6/2008 |
| JP | 2013-513716 A | 4/2013 |
| JP | 2016050280 A | 4/2016 |
| WO | WO-03/08180 A1 | 1/2003 |
| WO | WO-2004/085586 A2 | 10/2004 |
| WO | WO-2004/085600 A1 | 10/2004 |
| WO | WO-2004/111178 A1 | 12/2004 |
| WO | WO-2005/035382 A1 | 4/2005 |
| WO | WO-2006/020785 A1 | 2/2006 |
| WO | WO-2006/132680 A1 | 12/2006 |
| WO | WO-2006/132729 A1 | 12/2006 |
| WO | WO-2008/064014 A2 | 5/2008 |
| WO | WO-2008/087424 A1 | 7/2008 |
| WO | WO-2009/098659 A1 | 8/2009 |
| WO | WO-2009/152031 A1 | 12/2009 |
| WO | WO-2011/061628 A1 | 5/2011 |
| WO | WO-2012/087821 A1 | 6/2012 |
| WO | WO-2014/026856 A1 | 2/2014 |
| WO | WO-2014/066339 A1 | 5/2014 |
| WO | WO-2014/151718 A2 | 9/2014 |
| WO | WO-2016/055346 A1 | 4/2016 |
| WO | WO-2016/061025 A1 | 4/2016 |
| WO | WO-2016/061053 A1 | 4/2016 |
| WO | WO-2016/061054 A1 | 4/2016 |
| WO | WO-2016/061069 A2 | 4/2016 |
| WO | WO-2017/180888 A1 | 10/2017 |
| WO | WO-2017/218448 A1 | 12/2017 |
| WO | WO-2017/218449 A1 | 12/2017 |

OTHER PUBLICATIONS

Kotake H et al: "Film used as packaging material, contains polyvinyl alcohol with preset co-polymerization rate of vinyl unit containing anionic group, saponification degree and viscosity", WPI / THOMSON, vol. 2006, No. 22, Mar. 9, 2006 (Mar. 9, 2006). XP002753313.

Maitra et al., Cross-Linking in Hydrogels—A Review, *American Journal of Polymer Science*, 4(2):25-31 (2014).

Muller et al. (eds.), Perfumes: Art, Science and Technology, Springer Netherlands Publishing (1994).

Chinese Patent Application No. 201780036971.3, Notification of the First Office Action, dated Sep. 30, 2019.

International Search Report and Written Opinion, International Application No. PCT/US2017/036998, dated Aug. 16, 2017.

Canadian Patent Application No. 3001552, Office Action, dated Sep. 17, 2018.

WATER-SOLUBLE PACKETS

CROSS-REFERENCE TO RELATED APPLICATION

The benefit under 35 U.S.C. § 119(e) of U.S. Provisional Patent Application No. 62/349,440 filed Jun. 13, 2016, is hereby claimed, and the disclosure thereof is hereby incorporated by reference herein.

FIELD OF THE INVENTION

The present disclosure relates generally to water-soluble packets prepared from water-soluble films. In one aspect, the disclosure relates to packets having at least two water-soluble films, and methods of making such packets. In another aspect, the disclosure relates to water-soluble packets comprising at least two sealed compartments, the packet including two or more water-soluble films. The articles and methods can be associated with one or more benefits such as maintaining acceptable water-solubility and pouch strength while providing acceptable pouch seal strength, and/or providing an internal barrier suitable to prevent migration of a liquid composition from one packet compartment to another.

BACKGROUND

Water-soluble polymeric films are commonly used as packaging materials to simplify dispersing, pouring, dissolving and dosing of a material to be delivered. For example, pouches made from water-soluble film are commonly used to package compositions to be delivered to bulk water, for example, water-treatment agents for use with swimming pools. A consumer can directly add the pouched composition advantageously providing for accurate dosing while eliminating the need for the consumer to measure or otherwise handle the composition. The pouched composition may also reduce mess and potential skin contact that would be associated with dispensing a similar composition from a vessel, such as pouring a liquid agent from a bottle. In sum, soluble pre-measured polymeric film pouches provide for convenience of consumer use in a variety of applications.

Additionally, the COMMISSION REGULATION (EU) No. 1297/2014 of 5 Dec. 2014 amended, for the purposes of its adaptation to technical and scientific progress, Regulation (EC) No. 1272/2008 of the European Parliament and of the Council on classification, labeling and packaging of substances and mixtures to require additional provisions for liquid consumer laundry detergent in dosages for single use contained in a soluble packaging. Among those provisions were the requirements that the soluble packaging shall retain its liquid content for at least 30 seconds when the soluble packaging is placed in water at 20° C.

However, it has been found that some water-soluble films that would comply with COMMISSION REGULATION (EU) No. 1297/2014 and maintain acceptable solubility for packaging consumer products, when formed into liquid-containing pouches, exhibit poor pouch strength (e.g., burst when compressed under unacceptably low force), poor pouch sealing (e.g., the liquid leaks out of the pouch), and/or are unsuitable for use as barriers between two pouch compartments (e.g., a liquid component migrates through an inner film into a compartment containing a powder composition or a second liquid composition).

Thus, there exists a need in the art for a water soluble packet for holding liquid compositions that maintain acceptable pouch strength, pouch sealing, and/or barrier properties, without impairing the ultimate solubility of the water-soluble film.

SUMMARY

One aspect of the disclosure provides a water soluble pouch including at least two sealed compartments, the pouch including outer walls including water soluble film including a water soluble resin, and an inner wall including water soluble film including a water soluble resin, the outer wall films being sealed to the inner wall film, the outer wall films being characterized by: a dissolution time of 300 seconds or less in water at a temperature of 20° C. for an outer wall film having a thickness of about 76 micron in accordance with MonoSol Test Method MSTM-205, the water soluble resin of the outer wall films having a 4% solution viscosity at 20° C. in a range of 14.5 cP to 25 cP, and a pouch strength of at least 200 N as measured by the outer wall film sealed, conditioned, and tested according to the Pouch Strength Test and the inner wall film being characterized by: a dissolution time of 300 seconds or less in water at a temperature of 20° C. for an inner wall film having a thickness of about 76 micron in accordance with MonoSol Test Method MSTM-205, the water soluble resin of the inner film having a 4% solution viscosity at 20° C. in a range of 12 cP to 14.5 cP, and a tackiness value of at least 1500 g/s for an inner film tested according to the Tackiness PA Test.

Another aspect of the disclosure provides a water soluble pouch including at least two outer walls comprising water soluble film comprising a water soluble resin and at least one inner wall comprising water soluble film comprising a water soluble resin, the at least one inner wall having a first side and a second side and a thickness therebetween, the at least two outer wall films being sealed to the at least one inner wall film to form a compartment, wherein the at least two outer wall films are not sealed to the same side of the at least one inner wall such that at least two compartments are formed, the outer wall films being characterized by: a dissolution time of 300 seconds or less in water at a temperature of 20° C. for an outer wall film having a thickness of about 76 micron in accordance with MonoSol Test Method MSTM-205, the water soluble resin of the outer wall films having a 4% solution viscosity at 20° C. in a range of 14.5 cP to 25 cP, and a pouch strength of at least 200 N as measured by the outer wall film sealed and tested according to the Pouch Strength Test, and the inner wall film being characterized by: a dissolution time of 300 seconds or less in water at a temperature of 20° C. for an inner wall film having a thickness of about 76 micron in accordance with MonoSol Test Method MSTM-205, the water soluble resin of the inner film having a 4% solution viscosity at 20° C. in a range of 12 cP to 14.5 cP, and a tackiness value of at least 1500 g/s for an inner film tested according to the Tackiness PA Test.

Another aspect of the disclosure is a water soluble packet defining an interior pouch volume, the packet comprising at least two water-soluble films, wherein a film of the at least two water-soluble films comprises a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing, and wherein the water-soluble film comprising a polyvinyl alcohol copolymer comprising an anionic monomer unit is sealed to another film using a sealing solution comprising water, one or more diols and/or glycols, and a surfactant as further described herein.

Another aspect of the disclosure is a method of making a water-soluble pouch, comprising solvent sealing a first water-soluble film to a second water-soluble film, at least one of the films comprising a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing, and the sealing solution comprising water, one or more diols and/or glycols, and a surfactant as further described herein. For the compositions and methods described herein, optional features, including but not limited to components, compositional ranges thereof, substituents, conditions, and steps, are contemplated to be selected from the various aspects, embodiments, and examples provided herein.

Further aspects and advantages will be apparent to those of ordinary skill in the art from a review of the following detailed description. While the film, pouch, and their methods of making are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the present invention, two figures are appended hereto.

DETAILED DESCRIPTION

Figure 1:
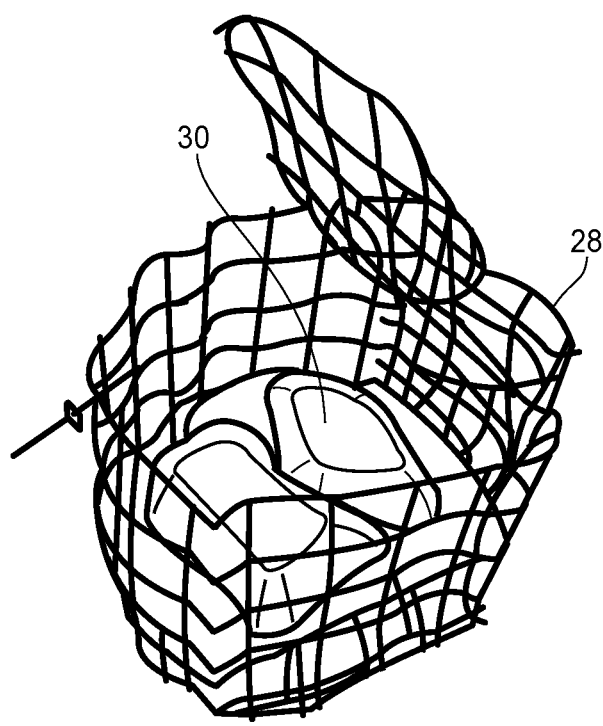
FIG. 1 is an illustration of a wire frame cage (shown with the top open, to better illustrate water-soluble pouches contained therein) for use in the Liquid Release Test described herein.

One aspect of the disclosure provides a water soluble pouch including at least two sealed compartments, the pouch including a first water soluble film disposed as outer walls, the first film including a water soluble resin, and a second water soluble film disposed as an inner wall, the second film including water soluble film including a water soluble resin, the outer wall films being sealed to the inner wall film. As used herein the first film is referred to as an outer wall film and the second film is referred to as an inner wall film, for convenience in connection with the embodiment wherein the second film is used as a partition wall. It will be recognized in the overall scope of the disclosure that the second film can be used as part of a two-film packet where the two films define a pouch volume therebetween. The outer wall films can be characterized by: a dissolution time of 300 seconds or less in water at a temperature of 20° C. for an outer wall film having a thickness of about 76 micron in accordance with MonoSol Test Method MSTM-205, the water soluble resin of the outer wall films can have a 4% solution viscosity at 20° C. in a range of 14.5 cP to 25 cP, and a pouch strength of at least 200 N as measured by the outer wall film sealed, conditioned, and tested according to the Pouch Strength Test. The second, inner wall film can be characterized by: a dissolution time of 300 seconds or less in water at a temperature of 20° C. for an inner wall film having a thickness of about 76 micron in accordance with MonoSol Test Method MSTM-205. The water soluble resin of the second, inner film can have a 4% solution viscosity at 20° C. in a range of 12 cP to 14.5 cP, and a tackiness value of at least 1500 g/s for an inner film tested according to the Tackiness PA Test.

Optionally, the outer wall film water soluble resin and/or inner wall film water soluble resin includes a polyvinyl alcohol or copolymer thereof. In embodiments, the outer wall film water soluble resin and/or inner wall film water soluble resin comprises a blend of a polyvinyl alcohol homopolymer and a polyvinyl alcohol copolymer comprising an anionic monomer unit. In embodiments, the anionic monomer unit comprises one or more of maleic acid, monoalkyl maleate, dialkyl maleate monomethyl maleate dimethyl maleate, maleic anhydride, alkali metal salts of the foregoing, esters of the foregoing, and combinations of the foregoing. Optionally, the outer wall film water soluble resin and/or inner wall film water soluble resin has a degree of hydrolysis in a range of 87 to 93, or if a blend of polyvinyl alcohol resins is used then the arithmetic weight average degree of hydrolysis is in a range of 87 to 93. In embodiments, the outer wall water soluble resin or resin blend can be not the same as the inner wall water soluble resin or resin blend. In embodiments, the outer wall water soluble resin or resin blend can differ from the inner wall water soluble resin or resin blend, such that at least one or more components of the water soluble resin or resin blend in the outer wall is not the same as at least one or more components of the resin or resin blend of the inner wall. In embodiments, the outer wall water soluble resin can be a resin blend and the inner wall water soluble resin can be a resin blend, and optionally at least one of the resins present in the outer wall water soluble resin blend is the same as one of the resins present in the inner wall water soluble resin blend.

The water soluble pouch may have at least two outer walls comprising water soluble film comprising a water soluble resin and at least one inner wall comprising water soluble film comprising a water soluble resin. The inner wall has a first side and a second side and a thickness therebetween, and the outer wall films are sealed to the at least one inner wall film to form a compartment with a defined interior volume between the outer wall and the inner wall. The outer wall films are not sealed to the same side of the inner wall such that at least two compartments are formed, each compartment having a defined interior volume. The defined interior volume may be the same or different for each compartment.

In embodiments, the inner wall film can have a thickness of at least 75 microns. Optionally, the thickness of each of the outer wall films does not vary from the thickness of the inner wall film by more than 10% if the films are non-thermoformed and does not vary by more than 50% (prior to thermoforming) if at least one film is thermoformed. In embodiments, the outer wall films and/or inner wall films can further contain a plasticizer. In embodiments, the outer wall films and/or inner wall films can further contain surfactant. In embodiments, the outer wall films and/or inner wall films can further contain an aversive agent.

Another aspect of the disclosure provides a water-soluble packet of the disclosure defining an interior pouch volume. One aspect of the disclosure is a water soluble packet defining an interior pouch volume, the packet comprising at least two water-soluble films. The films can include any of the resins, plasticizers, and other ingredients and characteristics described herein. In embodiments containing only two films sealed to each other and defining a volume therebetween, one film can have the characteristics of a first/outer wall film described below, and another film can have the characteristics of a second/inner wall film described below. A film of the at least two water-soluble films will include a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing. In one type of embodiment, both films will include a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing. The water-soluble film including a polyvinyl alcohol copolymer comprising an anionic monomer unit is solvent-sealed to another film using a sealing solution including water, one or more diols and/or glycols, and a surfactant as further described herein. The sealing solution optionally consists essentially of or consists of water, one or more diols and/or glycols, and a surfactant as further described herein.

The sealing solution surfactant can be one or more polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), and amine oxides, N-alkylbetaines and sulfobetaines (zwitterionics). Other suitable surfactants include dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof. In embodiments, the surfactant is selected from the group consisting of polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, and amine oxides, N-alkylbetaines, sulfobetaines, and combinations thereof, e.g. polyoxyethylenated polyoxypropylene glycol.

Another aspect of the disclosure is a method of making a water-soluble pouch, including solvent sealing a first water-soluble film to a second water-soluble film. At least one of the films includes a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing. In one type of embodiment, both films will include a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing. The sealing solution includes water, one or more diols and/or glycols, and a surfactant as further described herein. The sealing solution optionally consists essentially of or consists of water, one or more diols and/or glycols, and a surfactant as further described herein.

The sealing solution surfactant used in the method can be one or more polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), and amine oxides, N-alkylbetaines and sulfobetaines (zwitterionics). Other suitable surfactants include dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof. In embodiments, the surfactant is selected from the group consisting of polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, and amine oxides, N-alkylbetaines, sulfobetaines, and combinations thereof, e.g. polyoxyethylenated polyoxypropylene glycol.

In embodiments, the packet further includes a composition contained in the interior pouch volume. Optionally, the composition contained in the interior pouch volume is a liquid composition. Optionally, the liquid composition comprises a non-household composition selected from the group consisting of agricultural compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions, and combinations thereof.

In embodiments, the composition contained in the interior pouch volume can be a liquid and the packet can have a delayed release time of at least 30 seconds as measured by the Liquid Release Test described herein. In embodiments, the composition contained in the interior pouch volume can be a liquid and the packet can have a compression greater than 200 N as measured by the Pouch Strength Test described herein. In embodiments, the composition contained in the interior pouch volume can be a liquid and the packet can have a compression less than 2000 N, such as between 200 N and 2000 N as measured by the Pouch Strength Test.

"Comprising" as used herein means that various components, ingredients or steps that can be conjointly employed in practicing the present disclosure. Accordingly, the term "comprising" encompasses the more restrictive terms "consisting essentially of" and "consisting of." The present compositions can comprise, consist essentially of, or consist of any of the required and optional elements disclosed herein. For example, a thermoformed packet can "consist essentially of" a film described herein for use of it thermoforming characteristics, while including a non-thermoformed film (e.g., lid portion), and optional markings on the film, e.g. by inkjet printing. The invention illustratively disclosed herein suitably may be practiced in the absence of any element or step which is not specifically disclosed herein.

All percentages, parts and ratios referred to herein are based upon the total dry weight of the film composition or total weight of the packet content composition of the present disclosure, as the case may be, and all measurements made are at about 25° C., unless otherwise specified. All such weights as they pertain to listed ingredients are based on the active level and therefore do not include carriers or by-products that may be included in commercially available materials, unless otherwise specified.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

It is expressly contemplated that for any number value described herein, e.g. as a parameter of the subject matter described or part of a range associated with the subject matter described, an alternative which forms part of the description is a functionally equivalent range surrounding the specific numerical value (e.g. for a dimension disclosed as "40 mm" an alternative embodiment contemplated is "about 40 mm").

As used herein, the terms packet(s) and pouch(es) should be considered interchangeable. In certain embodiments, the terms packet(s) and pouch(es), respectively, are used to refer to a container made using the film and a fully-sealed container preferably having a material sealed therein, e.g., in the form a measured dose delivery system. The sealed pouches can be made from any suitable method, including such processes and features such as heat sealing and solvent sealing.

As used herein and unless specified otherwise, the terms "wt. %" and "wt %" are intended to refer to the composition of the identified element in "dry" (non water) parts by weight of the entire film, including residual moisture in the film (when applicable) or parts by weight of the entire composition enclosed within a pouch (when applicable).

As used herein and unless specified otherwise, the term "PHR" ("phr") is intended to refer to the composition of the identified element in parts per one hundred parts water-soluble polymer resin (whether PVOH or other polymer resins, unless specified otherwise) in the water-soluble film.

The film can be made by any suitable method, including a solution casting method. The film can be used to form a container (pouch) by any suitable process, including vertical form, fill, and sealing (VFFS), or thermoforming. The film can be sealed by any suitable process including, for example, solvent sealing or heat sealing of film layers, e.g. around a periphery of a container. The pouches can be used for dosing materials to be delivered into bulk water, for example.

The film, pouches, and related methods of making and use are contemplated to include embodiments including any combination of one or more of the additional optional elements, features, and steps further described below (including those shown in the Examples and Figures), unless stated otherwise.

In any embodiment, the water-soluble pouch can contain (enclose) a composition in the defined interior volume of the compartment formed by sealing the outer wall film to the inner wall film. The composition can be selected from a liquid, solid or combination thereof. As used herein, "liquid" includes free-flowing liquids, as well as pastes, gels, foams and mousses. Non-limiting examples of liquids include agricultural compositions, automotive compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions, including cleaning and detergent compositions applicable to any such use. Gases, e.g., suspended bubbles, or solids, e.g. particles, may be included within the liquids. A "solid" as used herein includes, but is not limited to, powders, agglomerates, and mixtures thereof. Non-limiting examples of solids include: granules, micro-capsules, beads, noodles, and pearlised balls. Solid compositions may provide a technical benefit including, but not limited to, through-the-wash benefits, pre-treatment benefits, and/or aesthetic effects.

Water-Soluble Film

The film and related pouches described herein comprise two or more water-soluble films. In one aspect, the two or more water-soluble films are PVOH films—each comprise a polyvinyl alcohol (PVOH) or modified polyvinyl alcohol resin. In embodiments, the two or more water-soluble films can each comprise a polyvinyl alcohol resin blend comprising a PVOH copolymer comprising an anionic monomer unit and one or more PVOH homopolymers. The film can have any suitable thickness, and a film thickness of about 76 microns ($\mu$m) is typical and particularly contemplated. Other values and ranges contemplated include values in a range of about 5 to about 200 $\mu$m, or in a range of about 20 to about 100 $\mu$m, or about 40 to about 90 $\mu$m, or about 50 to 80 $\mu$m, or about or about 60 to 65 $\mu$m for example 65 $\mu$m, 76 $\mu$m, or 88 $\mu$m. Without intending to be bound by theory, it is believed that the thickness of the inner wall film affects migration of liquid pouch compositions from one compartment to another. When the inner wall film is too thin under the circumstances, liquid compositions can migrate from one compartment to another through the inner partitioning wall. As inner wall film thickness increases, the film provides a better barrier to liquid composition migration. In embodiments, the inner film has a thickness of at least 75 micron. The outer wall thickness may be impacted by the manufacturing method chosen for making the water soluble pouch. If thermoforming is selected for making the water soluble pouch, the thickness of the outer wall film may be about 30 $\mu$m, about 35 $\mu$m, about 40 $\mu$m, about 45 $\mu$m, about 50 $\mu$m or about 55 $\mu$m.

PVOH Resin

Polyvinyl alcohol is a synthetic resin generally prepared by the alcoholysis, usually termed hydrolysis or saponification, of polyvinyl acetate. Fully hydrolyzed PVOH, where virtually all the acetate groups have been converted to alcohol groups, is a strongly hydrogen-bonded, highly crystalline polymer which dissolves only in hot water—greater than about 140° F. (about 60° C.). If a sufficient number of acetate groups are allowed to remain after the hydrolysis of polyvinyl acetate, that is the PVOH polymer is partially hydrolyzed, then the polymer is more weakly hydrogen-bonded, less crystalline, and is generally soluble in cold water—less than about 50° F. (about 10° C.). As such, the partially hydrolyzed polymer is a vinyl alcohol-vinyl acetate copolymer that is a PVOH copolymer, but is commonly referred to as PVOH.

As used herein, the term "homopolymer" generally includes polymers having a single type of monomeric repeating unit (e.g., a polymeric chain consisting of or consisting essentially of a single monomeric repeating unit). For the particular case of PVOH, the term "homopolymer" (or "PVOH homopolymer" or "PVOH polymer") further includes copolymers having a distribution of vinyl alcohol monomer units and vinyl acetate monomer units, depending on the degree of hydrolysis (e.g., a polymeric chain consisting of or consisting essentially of vinyl alcohol and vinyl acetate monomer units). In the limiting case of 100% hydrolysis, a PVOH homopolymer can include a true homopolymer having only vinyl alcohol units.

Water-soluble polymeric films based on PVOH can be subject to changes in solubility characteristics. The acetate group in the co-poly(vinyl acetate vinyl alcohol) polymer is known by those skilled in the art to be hydrolysable by either acid or alkaline hydrolysis. As the degree of hydrolysis increases, a polymer composition made from the PVOH homopolymer resin will have increased mechanical strength but reduced solubility at lower temperatures (e.g., requiring hot water temperatures for complete dissolution). Accordingly, exposure of a PVOH homopolymer resin to an alkaline environment (e.g., resulting from a laundry bleaching additive) can transform the resin from one which dissolves rapidly and entirely in a given aqueous environment (e.g., a cold water medium) to one which dissolves slowly and/or incompletely in the aqueous environment, potentially resulting in undissolved polymeric residue at the end of a wash cycle. This is an inherent weakness in the application of films based on just the vinyl acetate/alcohol co-polymer typified by commercial PVOH homopolymer resins.

PVOH copolymer resins with pendant carboxyl groups, such as, for example, vinyl alcohol/hydrolyzed methyl acrylate sodium salt resins, can form lactone rings between neighboring pendant carboxyl and alcohol groups, thus reducing the water solubility of the PVOH copolymer resin. In the presence of a strong base such as a laundry bleaching additive, the lactone rings can open over the course of several weeks at relatively warm (ambient) and high humidity conditions (e.g., via lactone ring-opening reactions to form the corresponding pendant carboxyl and alcohol groups with increased water solubility). Thus, contrary to the effect observed with PVOH homopolymer films, it is believed that such a PVOH copolymer film can become more soluble due to chemical interactions between the film and an alkaline composition inside the pouch during storage. Consequently, as they age, the packets may become increasingly prone to premature dissolution during a hot wash cycle (nominally 40° C.), and may in turn decrease the efficacy of certain laundry actives due to the presence of the bleaching agent and the resulting pH influence.

In embodiments, at least one of the outer wall water soluble film and/or inner wall soluble film includes a partially or fully hydrolyzed PVOH copolymer that includes an anionic monomer unit, a vinyl alcohol monomer unit, and optionally a vinyl acetate monomer unit. In embodiments, the anionic monomer unit comprises a maleic acid derived monomer. The maleic acid derived monomer can be one or more of maleic acid, monoalkyl maleate, dialkyl maleate, monomethyl maleate, dimethyl maleate, maleic anyhydride, alkali metal salts of the foregoing (e.g., sodium, potassium, or other alkali metal salts), esters of the foregoing (e.g., methyl, ethyl, or other $C_1$-$C_4$ or $C_6$ alkyl esters), and combinations thereof (e.g., multiple types of anionic monomers or equivalent forms of the same anionic monomer). For example, the maleic acid derived monomer can include one or more monoalkyl maleate, dialkyl maleate, and alkali metal salts thereof (e.g., sodium salts). Similarly, the anionic monomer can include one or more of monomethyl maleate, dimethyl maleate and alkali metal salts thereof (e.g., sodium salts).

In formulating a suitable packet for a given application (e.g., a composition-in-pouch article for treating bulk-water), multiple factors must be taken in to account. These factors include: (1) pouch strength, where a higher pouch strength translates into a more robust pouch that can withstand higher compression forces but may lead to sealing issues; (2) film tackiness, where a higher tackiness value desirably provides greater film sealability and a lower likelihood of pouch failure at the pouch seams; however, improved sealability often comes at the expense of pouch strength of the final product; and (3) dissolution residue, where a lower residue value desirably lessens the likelihood of residual film remaining when a pouch is exposed to aggressive conditions (e.g., low water and cold water conditions). Often, water-soluble polymer resins, whether PVOH or otherwise, may have suitable characteristics with respect to some of these factors, but they can have poor characteristics with respect to other of these factors. Accordingly, it would be desirable to provide a water-soluble film in which many, if not all, of these factors have favorable properties in the film.

Accounting for these factors, the present disclosure includes a water-soluble pouch comprising outer walls comprising water soluble film comprising a water soluble resin and an inner wall comprising water soluble film comprising a water soluble resin, the outer wall films being sealed to the inner wall film. In embodiments, the outer wall films and inner wall films can include a polyvinyl alcohol (PVOH) resin or polyvinyl alcohol resin blend and optionally one or more additional components including plasticizers, fillers, surfactants, and other additives as described in more detail below. Optionally, each of the outer wall films and/or the inner wall film can be characterized as being free or substantially free from other synthetic water-soluble polymers. As used herein, "substantially free" means that the PVOH resin or resin blend makes up at least 95 wt. %, at least 97 wt. %, at least 98%, or at least 99 wt. % of the total amount of synthetic water-soluble polymers in such water-soluble films. In embodiments wherein the outer wall films and/or the inner wall film is substantially free from other synthetic water-soluble polymers, the film can optionally include natural polymers (for example, starch, proteins, and guar gums) and/or semi-synthetic polymers (for example, starch derivatives and cellulose derivatives). In other aspects, the water-soluble films can include one or more additional water-soluble polymers. For example, the water-soluble film can include a PVOH resin blend including a third PVOH polymer, a fourth PVOH polymer, a fifth PVOH polymer, etc. (e.g., one or more additional PVOH homopolymers or PVOH copolymers, with or without anionic monomer units). For example, the water-soluble film can include at least a third (or fourth, fifth, etc.) water-soluble polymer which is other than a PVOH polymer (e.g., other than PVOH homopolymers or PVOH copolymers, with or without anionic monomer units), for example, a water soluble starch or modified starch.

The viscosity of a PVOH polymer ($\mu$) is determined by measuring a freshly made solution using a Brookfield LV type viscometer with UL adapter as described in British Standard EN ISO 15023-2:2006 Annex E Brookfield Test method. It is international practice to state the viscosity of 4% aqueous polyvinyl alcohol solutions at 20° C. All viscosities specified herein in Centipoise (cP) should be understood to refer to the viscosity of 4% aqueous polyvinyl alcohol solution at 20° C., unless specified otherwise. Similarly, when a resin is described as having (or not having) a particular viscosity, unless specified otherwise, it is intended that the specified viscosity is the average viscosity for the resin, which inherently has a corresponding molecular weight distribution.

When the PVOH resin of the outer and/or inner films is a PVOH resin blend, the outer and/or inner water-soluble film can be selected based upon the weighted log average viscosity ($\bar{\mu}$). The $\bar{\mu}$ for a PVOH resin that comprises two or more PVOH polymers is calculated by the formula $\bar{\mu}=e\Sigma W_i \cdot \ln\mu_i$, where, $\mu_i$ is the viscosity for the respective PVOH polymers.

For reference, the outer water-soluble film includes a first PVOH resin or resin blend denoted as having a first 4% solution viscosity at 20° C. ($\bar{\mu}_1$), and the inner water-soluble film includes a second PVOH resin or resin blend denoted as having a second 4% solution viscosity at 20° C. ($\bar{\mu}_2$). In various embodiments, the first viscosity $\bar{\mu}_1$ can be in a range of about 14.5 cP to about 25 cP, or about 14.5 cP to about 21 cP, or about 15.5 cP to about 20 cP, for example, about 14.5 cP, about 15 cP, about 16 cP, about 16.5 cP, about 17 cP, about 17.5 cP, about 18 cP, about 18.5 cP, about 19 cP, about 19.5 cP, about 20 cP, about 21 cP, about 22 cP, about 23 cP, about 24 cP, or about 25 cP. Alternatively or additionally, the second viscosity $\bar{\mu}_2$ can be in a range of about 12 cP to about 14.5 cP, for example about 12 cP, about 12.5 cP, about 13 cP, about 13.5 cP, or about 14.5 cP. It is well known in the art that the viscosity of PVOH resins is correlated with the weight average molecular weight ($\overline{Mw}$) of the PVOH resin, and often the viscosity is used as a proxy for the $\overline{Mw}$.

The PVOH resins can have a degree of hydrolysis (D.H. or DH) of at least 80%, 84% or 85% and at most about 99.7%, 98%, 96%, or 80%, for example in a range of about 84% to about 90%, or 85% to 88%, or 86.5%, or in a range of 85% to 99.7%, about 88% to 98%, or 90% to 96%, for example 90%, 91%, 92%, 93%, 94%, 95%, or 96%, or in a range of about 87 to 93. As used herein, the degree of hydrolysis is expressed as a mole percentage of vinyl acetate units converted to vinyl alcohol units.

Furthermore, when the PVOH resin is a PVOH resin blend, it is desirable to choose a PVOH resin blend that has an arithmetic weighted, average degree of hydrolysis ($\overline{H}°$) between about 80% and about 99.7%, between about 85 and about 98%, or between about 87 and about 93%, or about 96 and 98%, for example, about 85%, or about 86%, or about 87%, or about 87.5%, or about 88% or about 88.5%, or about 89%, or about 89.5%, or about 90%, or about 91%, or about 92%, or about 93%, or about 94%, or about 95%, or about 96%, or about 96.5%, or about 97%, or about 97.5%, or about 98%. For example, $\overline{H}°$ for a PVOH resin that comprises two or more PVOH polymers is calculated by the formula $\overline{H}°=\Sigma(Wi \cdot H_i)$ where $W_i$ is the weight percentage of the respective PVOH polymer and $H_i$ is the respective degrees of hydrolysis.

The water-soluble films that make up the water-soluble packets can include PVOH copolymers which can be a PVOH terpolymer including vinyl alcohol monomer units, vinyl acetate monomer units (i.e., when not completely hydrolyzed), and a single type of anionic monomer unit (e.g., a where a single type of monomer unit can include equivalent acid forms, salt forms, and optionally ester forms of the anionic monomer unit). In some aspects, the PVOH copolymer can include two or more types of anionic monomer units. General classes of anionic monomer units which can be used for the PVOH copolymer include the vinyl polymerization units corresponding to monocarboxylic acid vinyl monomers, their esters and anhydrides, dicarboxylic monomers having a polymerizable double bond, their esters and anhydrides, and alkali metal salts of any of the foregoing. Examples of suitable anionic monomer units include the vinyl polymerization units corresponding to vinyl anionic monomers including vinyl acetic acid, maleic acid, monoalkyl maleate, dialkyl maleate, maleic anhydride, fumaric acid, monoalkyl fumarate, dialkyl fumarate, fumaric anhydride, itaconic acid, monoalkyl itaconate, dialkyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, alkyl acrylates, alkyl alkacrylates, alkali metal salts of the foregoing, esters of the foregoing, and combinations of the foregoing.

In embodiments, the anionic monomer unit is selected from the group consisting of vinyl acetic acid, alkyl acrylates, maleic acid, monoalkyl maleate, dialkyl maleate, monomethyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts of the foregoing, esters of the foregoing, and combinations of the foregoing.

In one type of embodiment, the PVOH is a carboxyl group modified copolymer. In another aspect, the PVOH can be modified with a dicarboxyl type monomer. In one class of these embodiments, the α carbon of both carbonyls are connected to the unsaturated bond (e.g., maleic acid, fumaric acid). In another class of these embodiments, the α carbon of both carbonyls are connected to the unsaturated bond and the unsaturated bond is further substituted, e.g., with a methyl branch (e.g., citraconic acid, mesaconic acid). In another class of these embodiments, the β carbon of one carbonyl and the α carbon of the other carbonyl are connected to the unsaturated bond (e.g., itaconic acid, cis-glutaconic acid, trans-glutaconic acid). Monomers that provide alkyl carboxyl groups are contemplated. A maleic acid type (e.g., maleic acid, dialkyl maleate (including dimethyl maleate), monoalkyl maleate (including monomethyl maleate), or maleic anhydride) comonomer is particularly contemplated. In embodiments, the anionic monomer unit is selected from the group consisting of maleic acid, monoalkyl maleate, dialkyl maleate, monomethyl maleate, dimethyl maleate, maleic anhydride, alkali metal salts of the foregoing, and combinations thereof.

When the PVOH resin comprises a PVOH copolymer including an anionic monomer, the level of incorporation of the one or more anionic monomer units in the PVOH copolymer is not particularly limited. In embodiments, the one or more anionic monomer units are present in the PVOH copolymer in an amount in a range of about 1 mol. % to 10 mol. %, or 1.5 mol. % to about 8 mol. %, or about 2 mol. % to about 6 mol. %, or about 3 mol. % to about 5 mol. %, or about 1 mol. % to about 4 mol. % (e.g., at least 1.0, 1.5, 2.0, 2.5, 3.0, 3.5, or 4.0 mol. % and/or up to about 3.0, 4.0, 4.5, 5.0, 6.0, 8.0, or 10 mol. % in various embodiments).

PVOH copolymers including anionic monomers can also be characterized by the level of pendant anionic groups present in the copolymer. The level of pendant anionic groups in the PVOH copolymers is not particularly limited. In embodiments, the pendant anionic groups are present in the PVOH copolymer in an amount in a range of about 1% to 20%, or 1.5% to 8%, or 2% to 12%, or 2% to 10%, or at least 2.5%, or at least 3%, or at least 3.5%, for example 2%, 3%, 6%, or 8%.

The water-soluble film can contain at least about 50 wt. %, 55 wt. %, 60 wt. %, 65 wt. %, 70 wt. %, 75 wt. %, 80 wt. %, 85 wt. %, or 90 wt. % and/or up to about 60 wt. %, 70 wt. %, 80 wt. %, 90 wt. %, 95 wt. %, or 99 wt. % of the PVOH resin or resin blend. In embodiments, the outer wall film comprises a blend of a polyvinyl alcohol homopolymer and a polyvinyl alcohol copolymer comprising an anionic monomer unit. The first/outer wall blend can comprise the polyvinyl alcohol copolymer comprising an anionic monomer unit in an amount in a range of about 30 wt. % to about 100 wt. % (or about 30 wt. % to about 70 wt. %, about 30 wt. % to about 65 wt. %, or about 30 wt. % to about 50 wt. %, or about 30 wt. % to about 40 wt. %, or about 65 wt. % to about 99 wt. %, or greater than 65 wt. % to 99 wt. %, or 70 wt. %, to 99 wt. %) based on the total weight of the polyvinyl alcohol (i.e., homopolymers and copolymers) in the film (blend). The outer wall blend can further comprise from 0 to 70 weight % (or 1 wt. % to 35 wt. %, or 1 wt. % to less than 35 wt. %, or 1 wt. % to 30 wt. %, or about 30 wt. % to about 70 wt. %, or about 35 wt. % to about 70 wt. %, or about 50 wt. % to about 70 wt. %, or about 60 wt. % to about 70 wt. %) of a polyvinyl alcohol homopolymer, based on the total weight of the polyvinyl alcohol in the film (blend). In embodiments, the inner wall film comprises a blend of a polyvinyl alcohol homopolymer and a polyvinyl alcohol copolymer comprising an anionic monomer unit. The second/inner wall blend can comprise the polyvinyl alcohol copolymer comprising an anionic monomer unit in an amount in a range of about 30 wt. % to about 100 wt. % (or about 30 wt. % to about 70 wt. %, about 30 wt. % to about 65 wt. %, or about 30 wt. % to about 50 wt. %, or about 30 wt. % to about 40 wt. %, or about 65 wt. % to about 99 wt. %, or greater than 65 wt. % to 99 wt. %, or 70 wt. %, to 99 wt. %) based on the total weight of the polyvinyl alcohol (i.e., homopolymers and copolymers) in the film (blend). The inner wall blend can further comprise from 0 to 70 weight % (or 1 wt. % to 35 wt. %, or 1 wt. % to less than 35 wt. %, or 1 wt. % to 30 wt. %, or about 30 wt. % to about 70 wt. %, or about 35 wt. % to about 70 wt. %, or about 50 wt. % to about 70 wt. %, or about 60 wt. % to about 70 wt. %) of a polyvinyl alcohol homopolymer, based on the total weight of the polyvinyl alcohol in the film (blend). In embodiments, the foregoing weight percents of PVOH copolymer and PVOH homopolymer alternatively or additionally can be relative to total water-soluble polymer content in film, PVOH or otherwise.

In another aspect of the water-soluble film, the PVOH resin or resin blend is selected for the inner wall film such that the resulting water-soluble film and pouches made therefrom have maintained or improved solubility while providing multi-compartment pouches that have good sealability. In particular, the inner wall water-soluble film has the property in which (a) the water-soluble film has a residue value of about 52 wt. % or less, about 50 wt. % or less, or about 48 wt. % or less as measured by the Dissolution Chamber Test (described below). In some embodiments, the inner wall water-soluble film has the property in which (b1) the water-soluble resin (or resin blend) that makes up the film has a viscosity (or log weight average viscosity) in a range of 12 cp to 14.5 cp, as described above. In some embodiments, the inner water-soluble film has the property in which (c) the water-soluble film has a tackiness value of at least about 1500 g/s, or at least about 1800 g/s, or at least about 2000 g/s as measured by the Tackiness PA Test (described below). In various embodiments, the water-soluble film has the properties (a) and (b), (a) and (c), (b) and (c), or (a) and (b) and (c).

In another aspect of the water-soluble film, the PVOH resin or resin blend is selected for the outer wall films such that the resulting water-soluble film and pouches made therefrom have maintained or improved solubility while providing multi-compartment pouches that have good pouch strength. In particular, the outer wall water-soluble films have the property in which (a) the water-soluble film has a residue value of about 52 wt. % or less, about 50 wt. % or less, or about 48 wt. % or less as measured by the Dissolution Chamber Test (described below). In some embodiments, the outer wall water-soluble films have the property in which (b2) the water-soluble resin (or resin blend) that makes up the film has a viscosity (or log weight average viscosity) in a range of 14.5 cp to 23 cp, as described above. In some embodiments, the outer water-soluble films have the property in which (d) when the outer wall water soluble film is formulated into a single compartment pouch, the pouch has a strength of at least 200 N as determined by the Pouch Strength Test (described below). In various embodiments, the water-soluble film has the properties (a) and (b2), (a) and (d), (b2) and (d), or (a) and (b2) and (d).

The PVOH resin blends according to the disclosure unexpectedly permit the formulation of water-soluble films having a combination of desirable physical and chemical properties, even when the PVOH homopolymer or copolymer included in the resin blends are deficient individually with respect to one or more of physical or chemical properties. For example, each PVOH homopolymer or copolymer in the blend can have at least one undesirable trait for a particular property, but the water-soluble film incorporating the blend achieves a desirable trait for the particular property of each PVOH homopolymer or copolymer.

Other Water Soluble Polymers

Other water soluble polymers for use in addition to the first and second PVOH copolymers can include, but are not limited to a vinyl alcohol-vinyl acetate copolymer, sometimes referred to as a PVOH homopolymer, polyacrylates, water-soluble acrylate copolymers, polyvinyl pyrrolidone, polyethyleneimine, pullulan, water-soluble natural polymers including, but not limited to, guar gum, gum Acacia, xanthan gum, carrageenan, and starch, water-soluble polymer derivatives including, but not limited to, modified starches, ethoxylated starch, hydroxyethylated starch and hydroxypropylated starch, copolymers of the forgoing and combinations of any of the foregoing. Yet other water-soluble polymers can include polyalkylene oxides, polyacrylamides, polyacrylic acids and salts thereof, celluloses, cellulose ethers, cellulose esters, cellulose amides, polyvinyl acetates, polycarboxylic acids and salts thereof, polyaminoacids, polyamides, gelatines, methylcelluloses, carboxymethylcelluloses and salts thereof, dextrins, ethylcelluloses, hydroxyethyl celluloses, hydroxypropyl methylcelluloses, maltodextrins, polymethacrylates, and combinations of any of the foregoing. Such water-soluble polymers, whether PVOH or otherwise are commercially available from a variety of sources.

The water-soluble film can contain other auxiliary agents and processing agents, such as, but not limited to, plasticizers, plasticizer compatibilizers, surfactants, lubricants, release agents, fillers, extenders, cross-linking agents, antiblocking agents, antioxidants, detackifying agents, antifoams, nanoparticles such as layered silicate-type nanoclays (e.g., sodium montmorillonite), bleaching agents (e.g., sodium metabisulfite, sodium bisulfite or others), aversive agents such as bitterants (e.g., denatonium salts such as denatonium benzoate, denatonium saccharide, and denatonium chloride; sucrose octaacetate; quinine; flavonoids such as quercetin and naringen; and quassinoids such as quassin and brucine) and pungents (e.g., capsaicin, piperine, allyl isothiocyanate, and resinferatoxin), and other functional ingredients, in amounts suitable for their intended purposes. Embodiments including plasticizers are preferred. The amount of such agents can be up to about 50 wt. %, 20 wt %, 15 wt %, 10 wt %, 5 wt. %, 4 wt % and/or at least 0.01 wt. %, 0.1 wt %, 1 wt %, or 5 wt %, individually or collectively.

Plasticizers

A plasticizer is a liquid, solid, or semi-solid that is added to a material (usually a resin or elastomer) making that material softer, more flexible (by decreasing the glass-transition temperature of the polymer), and easier to process. A polymer can alternatively be internally plasticized by chemically modifying the polymer or monomer. In addition or in the alternative, a polymer can be externally plasticized by the addition of a suitable plasticizing agent.

The plasticizer can include, but is not limited to, glycerin, diglycerin, sorbitol, ethylene glycol, diethylene glycol, triethylene glycol, dipropylene glycol, tetraethylene glycol, propylene glycol, polyethylene glycols up to 400 MW, neopentyl glycol, trimethylolpropane, polyether polyols, sorbitol, 2-methyl-1,3-propanediol (MPDiol®), ethanolamines, and a mixture thereof. A preferred plasticizer is glycerin, sorbitol, triethyleneglycol, propylene glycol, dipropylene glycol, 2-methyl-1,3-propanediol, trimethylolpropane, or a combination thereof. The total amount of the plasticizer can be in a range of about 10 wt. % to about 45 wt. %, or about 15 wt. % to about 35 wt. %, or about 20 wt. % to about 30 wt. %, or about 20 wt. % to about 45 wt. %, for example about 25 wt. %, based on total film weight. In embodiments, the amount of plasticizer in the water-soluble film is expressed in parts per 100 parts total water soluble polymer (PHR) in the water-soluble film and is present at least 30 PHR, or at least 35 PHR, for example. The total amount of plasticizer can be up to 40 PHR or 45 PHR or 50 PHR, for example. The total amount of plasticizer can be in a range of 30-50 PHR, about 32.5 PHR to about 42.5 PHR, or 35-45 PHR, or 35-40 PHR, or greater than 30 PHR and less than 45 PHR, or 40 PHR to 50 PHR, for example. The total amount of plasticizer can be 34 or 37.5 PHR.

Combinations of glycerin, trimethylol propane, and sorbitol can be used. Optionally, glycerin can be used in an amount of about 5 wt % to about 30 wt %, or 5 wt % to about 20 wt %, e.g., about 13 wt %. Optionally, trimethylol propane can be used in an amount of about 1 wt. % to about 20 wt. %, or about 3 wt. % to about 10 wt. %, or about 1 wt. % to about 5 wt. %, for example 3 wt. %, or 6 wt. %. Optionally, sorbitol can be used in an amount of about 1 wt % to about 20 wt %, or about 2 wt % to about 18 wt %, or about 5 wt. % to about 15 wt. %, or about 8 wt. % to about 13 wt. %, e.g., about 10 wt %. The specific amounts of plasticizers can be selected in a particular embodiment based on desired film flexibility and processability features of the water-soluble film. At low plasticizer levels, films may become brittle, difficult to process, or prone to breaking. At elevated plasticizer levels, films may be too soft, weak, or difficult to process for a desired use.

Surfactants

Surfactants for use in water-soluble films are well known in the art. Optionally, surfactants are included to aid in the dispersion of the resin solution upon casting. Suitable surfactants can include the nonionic, cationic, anionic and zwitterionic classes. Suitable surfactants include, but are not limited to, polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), and amine oxides, N-alkylbetaines and sulfobetaines (zwitterionics). Other suitable surfactants include dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, and combinations thereof. In embodiments, the surfactant is selected from the group consisting of polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, and amine oxides, N-alkylbetaines, sulfobetaines, and combinations thereof.

In various embodiments, the amount of surfactant in the water-soluble film is in a range of about 0.1 wt % to about 8.0 wt %, or about 1.0 wt % to about 7.0 wt %, or about 3 wt % to about 7 wt %, or about 5 wt % to about 7 wt %. In embodiments, the amount of surfactant in the water-soluble film is expressed in parts per 100 parts total water soluble polymer (phr) in the water-soluble film and is present in a range of about 0.5 phr to about 12 phr, about 1.0 phr to about 11.0 phr, about 3.0 phr to about 10.5 phr, or about 1.0 phr to about 2.0 phr.

Suitable lubricants/release agents can include, but are not limited to, fatty acids and their salts, fatty alcohols, fatty esters, fatty amines, fatty amine acetates and fatty amides. Preferred lubricants/release agents are fatty acids, fatty acid salts, and fatty amine acetates. In one type of embodiment, the amount of lubricant/release agent in the water-soluble film is in a range of about 0.02 wt % to about 1.5 wt %, optionally about 0.1 wt % to about 1 wt %.

Suitable fillers/extenders/antiblocking agents/detackifying agents include, but are not limited to, starches, modified starches, crosslinked polyvinylpyrrolidone, crosslinked cellulose, microcrystalline cellulose, silica, metallic oxides, calcium carbonate, talc, mica, stearic acid and metal salts thereof, for example, magnesium stearate. Preferred materials are starches, modified starches and silica. In one type of embodiment, the amount of filler/extender/antiblocking agent/detackifying agent in the water soluble film can be in a range of about 1 wt. % to about 6 wt. %, or about 1 wt. % to about 4 wt. %, or about 2 wt. % to about 4 wt. %, or about 1 phr to about 6 phr, or about 1 phr to about 4 phr, or about 2 phr to about 4 phr, for example.

An anti-block agent (e.g. $SiO_2$ and/or stearic acid)) can be present in the film in an amount of at least 0.1 PHR, or at least 0.5 PHR, or at least 1 PHR, or in a range of about 0.1 to 5.0 PHR, or about 0.1 to about 3.0 PHR, or about 0.4 to 1.0 PHR, or about 0.5 to about 0.9 PHR, or about 0.5 to about 2 PHR, or about 0.5 to about 1.5 PHR, or 0.1 to 1.2 PHR, or 0.1 to 4 PHR, for example 0.5 PHR, 0.6 PHR, 0.7 PHR, 0.8 PHR, or 0.9 PHR.

If the anti-block agent is an $SiO_2$ particle, a suitable median particle size for the anti-block agent includes a median size in a range of about 3 or about 4 microns to about 11 microns, or about 4 to about 8 microns, or about 5 to about 6 microns, for example 5, 6, 7, 8, or 8 microns. A suitable $SiO_2$ is an untreated synthetic amorphous silica designed for use in aqueous systems.

The water-soluble film can further have a residual moisture content of at least 4 wt. %, for example in a range of about 4 to about 10 wt. %, as measured by Karl Fischer titration.

Method of Making Film

One contemplated class of embodiments is characterized by the water-soluble film of the water-soluble packets being formed by, for example, solvent casting. Processes for solvent casting of PVOH are well-known in the art. For example, in the film-forming process, the polyvinyl alcohol polymers and secondary additives are dissolved in a solvent, typically water, metered onto a surface, allowed to substantially dry (or force-dried) to form a cast film, and then the resulting cast film is removed from the casting surface. The process can be performed batchwise, and is more efficiently performed in a continuous process.

In the formation of continuous films of polyvinyl alcohol, it is the conventional practice to meter a solution of the solution onto a moving casting surface, for example, a continuously moving metal drum or belt, causing the solvent to be substantially removed from the liquid, whereby a self-supporting cast film is formed, and then stripping the resulting cast film from the casting surface.

Optionally, the water-soluble film can be a free-standing film consisting of one layer or a plurality of like layers.

Pouches

The film disclosed herein is useful for creating pouches to contain a composition therein. The pouch composition may take any form such as powders, gels, pastes, liquids, tablets or any combination thereof. The film is also useful for any other application in which improved wet handling and low cold water residues are desired.

The outer wall film and inner wall film described herein can be used to make a water soluble pouch with two or more compartments and may be used in combination with other films of other polymeric materials. Additional films can, for example, be obtained by casting, blow-molding, extrusion or blown extrusion of the same or a different polymeric material as one layer or plurality of layers (laminate), as known in the art. One contemplated class of embodiments is characterized by at least two films of the pouch being cast films. In one type of embodiment, the polymers, copolymers or derivatives thereof suitable for use as the additional film are selected from polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthan, and carrageenans. For example, polymers can be selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and combinations thereof, or selected from polyvinyl alcohols, polyvinyl alcohol copolymers and hydroxypropyl methyl cellulose (HPMC), and combinations thereof. One contemplated class of embodiments is characterized by the level of polymer in the packet material, for example the PVOH copolymer described above, as described above, being at least 60%.

The pouches of the present disclosure can include at least two sealed compartments. A water-soluble pouch can be formed from two outer wall films being sealed to different sides of an inner wall film at an interface, such as a first side (interface) and a second side (interface) of the inner wall film to form two compartments, each compartment having a defined internal volume. The sealed compartments define an internal volume capable of enclosing a composition. Accordingly, a "sealed compartment" encompasses sealed compartments wherein the outer film includes a vent hole, for example, in embodiments wherein the compartment encloses a solid that off-gasses. In embodiments, one or both of the outer wall films include a PVOH film described above. In embodiments, the inner wall films include a PVOH film described above. The films define at least two interior pouch container volumes which contain any desired composition for release into an aqueous environment. The composition is not particularly limited, for example including any of the variety of compositions described herein. In embodiments comprising multiple compartments, each compartment may contain identical and/or different compositions. In turn, the compositions may take any suitable form including, but not limited to liquid, solid and combinations thereof (e.g. a solid suspended in a liquid). In embodiments, the pouches comprises a first, second and third compartment, each of which respectively contains a different first, second, and third composition.

The compartments of multi-compartment pouches may be of the same or different size(s) and/or volume(s). In embodiments, a third and/or subsequent compartment is superimposed on one of the first or second compartments. In one embodiment, the third compartment may be superimposed on the second compartment, which is in turn superimposed on the first compartment in a sandwich configuration. However it is also equally envisaged that the optionally third and subsequent compartments may be attached in a side by side relationship by sealing an outer wall film to the inner wall film in multiple locations (interfaces) to create two or more side by side defined internal volumes.

The geometry of the compartments may be the same or different. In embodiments the optionally third and subsequent compartments each have a different geometry and shape as compared to the first and second compartment. In these embodiments, the optionally third and subsequent compartments are arranged in a design on the first or second compartment. The design may be decorative, educative, or illustrative, for example to illustrate a concept or instruction, and/or used to indicate origin of the product.

The pouches of the present disclosure may comprise one or more different films. In multiple compartment embodiments, the packet may be made from one or more films such that any given packet compartment may comprise walls made from a single film or multiple films having differing compositions. In one embodiment, a multi-compartment pouch comprises at least three walls: an outer upper wall; an outer lower wall; and a partitioning wall. The outer upper wall and the outer lower wall are generally opposing and form the exterior of the pouch. The inner wall partitions the pouch and is secured to the generally opposing outer walls along a seal line. The partitioning wall separates the interior of the multi-compartment pouch into at least a first compartment and a second compartment.

Pouches and packets may be made using any suitable equipment and method. The film may be dampened, and/or heated to increase the malleability thereof. The method may also involve the use of a vacuum to draw the film into a suitable mold. The vacuum drawing the film into the mold can be applied for about 0.2 to about 5 seconds, or about 0.3 to about 3, or about 0.5 to about 1.5 seconds, once the film is on the horizontal portion of the surface. This vacuum can be such that it provides an under-pressure in a range of 10 mbar to 1000 mbar, or in a range of 100 mbar to 600 mbar, for example.

The molds, in which packets may be made, can have any shape, length, width and depth, depending on the required dimensions of the pouches. The molds may also vary in size and shape from one to another, if desirable. For example, the volume of the final pouches may be about 5 ml to about 300 ml, or about 10 to 150 ml, or about 20 to about 100 ml, and that the mold sizes are adjusted accordingly.

In one embodiment, the packet comprises a first and a second sealed compartment. The second compartment is in a generally superposed relationship with the first sealed compartment such that the second sealed compartment and the first sealed compartment share a partitioning wall interior to the pouch.

In embodiments, the first compartment and the second compartment can each contain a composition. The first composition and the second composition are selected from one of the following combinations: liquid, liquid; liquid, powder; powder, powder; and powder, liquid. In embodiments, at least one of the first and second compositions can be a liquid. In embodiments, both the first and the second compositions can be liquid. The first and second composition may be the same or different.

In some embodiments, the composition may be selected from the group of liquid light duty and liquid heavy duty liquid detergent compositions, powdered detergent compositions, dish detergent for hand washing and/or machine washing; hard surface cleaning compositions, fabric enhancers, detergent gels commonly used for laundry, and bleach and laundry additives, shampoos, and body washes. agricultural compositions, automotive compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions, including cleaning and detergent compositions applicable to any such use.

Shaping, Sealing, and Thermoforming

A thermoformable film is one that can be shaped through the application of heat and a force.

As is known in the art, thermoforming a film is the process of heating the film, shaping it (e.g. in a mold), and then allowing the film to cool, whereupon the film will hold its shape, e.g. the shape of the mold. The heat may be applied using any suitable means. For example, the film may be heated directly by passing it under a heating element or through hot air, prior to feeding it onto a surface or once on a surface. Alternatively, it may be heated indirectly, for example by heating the surface or applying a hot item onto the film. In embodiments, the film is heated using an infrared light. The film may be heated to a temperature in a range of about 50 to about 150° C., about 50 to about 120° C., about 60 to about 130° C., about 70 to about 120° C., or about 60 to about 90° C. Thermoforming can be performed by any one or more of the following processes: the manual draping of a thermally softened film over a mold, or the pressure induced shaping of a softened film to a mold (e.g., vacuum forming), or the automatic high-speed indexing of a freshly extruded sheet having an accurately known temperature into a forming and trimming station, or the automatic placement, plug and/or pneumatic stretching and pressuring forming of a film.

Alternatively, the film can be wetted by any suitable means, for example directly by spraying a wetting agent (including water, a solution of the film composition, a plasticizer for the film composition, or any combination of the foregoing) onto the film, prior to feeding it onto the surface or once on the surface, or indirectly by wetting the surface or by applying a wet item onto the film.

Once a film has been heated and/or wetted, it may be drawn into an appropriate mold, preferably using a vacuum. The filling of the molded film can be accomplished by utilizing any suitable means. In embodiments, the most preferred method will depend on the product form and required speed of filling. In embodiments, the molded film is filled by in-line filling techniques. The filled, open packets are then closed forming the pouches, using a second film, by any suitable method. This may be accomplished while in horizontal position and in continuous, constant motion. The closing may be accomplished by continuously feeding a second film, preferably water-soluble film, over and onto the open packets and then preferably sealing the first and second film together, typically in the area between the molds and thus between the packets.

Any suitable method of sealing the packet and/or the individual compartments thereof may be utilized. Non-limiting examples of such means include heat sealing, solvent welding, solvent or wet sealing, and combinations thereof. Typically, only the area which is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying solvent onto the area between the molds, or on the closing material, by for example, spraying or printing this onto these areas, and then applying pressure onto these areas, to form the seal. Sealing rolls and belts as described above (optionally also providing heat) can be used, for example.

In embodiments, the inner film is sealed to the outer films by solvent sealing. The sealing solution is generally an aqueous solution. In embodiments, the sealing solution comprises water. In embodiments, the sealing solution comprises water and further includes one or more diols and/or glycols such as 1,2-ethanediol (ethylene glycol), 1,3-propanediol, 1,2-propanediol, 1,4-butanediol (tetramethylene glycol), 1,5-pantanediol (pentamethylene glycol), 1,6-hexanediol (hexamethylene glycol), 2,3-butanediol, 1,3-butanediol, 2-methyl-1,3-propanediol, various polyethylene glycols (e.g., diethylene glycol, triethylene glycol), and combinations thereof. In embodiments, the sealing solution comprises erythritol, threitol, arabitol, xylitol, ribitol, mannitol, sorbitol, galactitol, fucitol, iditol, inositol, volemitol, isomal, maltitol, lactitol. In embodiments, the sealing solution comprises a surfactant. Suitable surfactants include surfactants previously disclosed herein.

The sealing solution can be applied to the interfacial areas of the inner film in any amount suitable to adhere the inner and outer films. As used herein, the term "coat weight" refers to the amount of sealing solution applied to the film in grams of solution per square meter of film. In general, when the coat weight of the sealing solvent is too low, the films do not adequately adhere and the risk of pouch failure at the seams increases. Further, when the coat weight of the sealing solvent is too high, the risk of the solvent migrating from the interfacial areas increases, increasing the likelihood that etch holes may form in the sides of the pouches. The coat weight window refers to the range of coat weights that can be applied to a given film while maintaining both good adhesion and avoiding the formation of etch holes. A broad coat weight window is desirable as a broader window provides robust sealing under a broad range of operations. Suitable coat weight windows are at least about 3 g/m², or at least about 4 g/m², or at least about 5 g/m², or at least about 6 g/m².

The formed pouches may be cut by a cutting device. Cutting can be accomplished using any suitable method. It may be preferred that the cutting is also done in continuous manner, and preferably with constant speed and preferably while in horizontal position. The cutting device can, for example, be a sharp item, or a hot item, or a laser, whereby in the latter cases, the hot item or laser 'burns' through the film/sealing area.

In embodiments, pouches may be made according to a process comprising the steps of: a) forming a first compartment, optionally using heat and/or vacuum, using a first film on a first forming machine; b) filling the first compartment with a first composition; c) closing the first compartment by means of a second film, thereby forming a first closed pouch compartment; d) on a second forming machine, deforming a second film, optionally using heat and vacuum, to make a second molded compartment; d) filling the second compartments; and e) sealing the second compartment using the second film side of the first closed pouch compartment. Suitable processes may be found in U.S. Patent Application Publication No. 2013/0240388 A1, herein incorporated by reference in its entirety.

In embodiments, second, and/or third compartment(s) can be made in a separate step and then combined with the first compartment as described in U.S. Patent Application Publication No. 2014/345064 A1 or U.S. Patent Application Publication No. 2009/312220 A1.

It should be understood that by the use of appropriate feed stations, it may be possible to manufacture multi-compartment pouches incorporating a number of different or distinctive compositions and/or different or distinctive liquid, gel or paste compositions.

In embodiments, the film and/or pouch is sprayed or dusted with a suitable material, such as an active agent, a lubricant, an aversive agent, or mixtures thereof. In embodiments, the film and/or pouch is printed upon, for example, with an ink and/or an active agent.

Pouch Contents

The present articles (e.g., in the form of pouches or packets) may contain various compositions, for example non-household care compositions. A multi-compartment pouch may contain the same or different compositions in each separate compartment. The composition is proximal to the water-soluble film. The composition may be less than about 10 cm, or less than about 5 cm, or less than about 1 cm from the film. Typically the composition is adjacent to the film or in contact with the film. The film may be in the form of a pouch or a compartment, containing the composition therein.

The inner film of the pouch may be utilized to keep compositions containing incompatible ingredients physically separated or partitioned from each other. It is believed that such partitioning may expand the useful life and/or decrease physical instability of such ingredients. Additionally or alternatively, such partitioning may provide aesthetic benefits as described in U.S. Pat. No. 8,835,372.

A fabric or household care composition includes fabric treatments, hard surfaces, air care, car care, dishwashing, fabric conditioning and softening, laundry detergency, laundry and rinse additive and/or care, hard surface cleaning and/or treatment, and other cleaning for consumer or institutional use. Non-household care compositions are for other uses.

Non-limiting examples of other useful compositions (e.g., non-household care compositions) include agricultural compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions, including cleaning and detergent compositions applicable to any such use while excluding fabric and household care compositions. Compositions of use in the present pouches may take the form of a liquid, solid or a powder. Liquid compositions may comprise a solid. Solids may include powder or agglomerates, such as micro-capsules, beads, noodles or one or more pearlized balls or mixtures thereof. Such a solid element may provide a technical benefit, through the wash or as a pre-treat, delayed or sequential release component; additionally or alternatively, it may provide an aesthetic effect.

It is contemplated that one type of embodiment will include an article as described herein with a sealed compartment containing a fabric care or household care composition, a film including a blend of a polyvinyl alcohol homopolymer and an anionic polyvinyl alcohol copolymer, and both the first water soluble film and the second water soluble film include blends include 65 wt. % or greater of an anionic polyvinyl alcohol copolymer.

It is contemplated that another type of embodiment will include an article as described herein with a sealed compartment containing a fabric care or household care composition, a film including a blend of at least two anionic polyvinyl alcohol copolymers, and both then first water soluble film and the second water soluble film include blends of at least two anionic polyvinyl alcohol copolymers.

The compositions encapsulated by the films described herein can have any suitable viscosity depending on factors such as formulated ingredients and purpose of the composition. In one embodiment, the composition has a high shear viscosity value, at a shear rate of 20 s$^{-1}$ and a temperature of 20° C., of 100 to 3,000 cP, alternatively 300 to 2,000 cP, alternatively 500 to 1,000 cP, and a low shear viscosity value, at a shear rate of 1 s$^{-1}$ and a temperature of 20° C., of 500 to 100,000 cP, alternatively 1000 to 10,000 cP, alternatively 1,300 to 5,000 cP. Methods to measure viscosity are known in the art. According to the present invention viscosity measurements are carried out using a rotational rheometer e.g. TA instruments AR550. The instrument includes a 40 mm 2° or 1° cone fixture with a gap of around 50-60 μm for isotropic liquids, or a 40 mm flat steel plate with a gap of 1000 μm for particles containing liquids. The measurement is carried out using a flow procedure that contains a conditioning step, a peak hold and a continuous ramp step. The conditioning step involves the setting of the measurement temperature at 20° C., a pre-shear of 10 seconds at a shear rate of 10 s$^{-1}$, and an equilibration of 60 seconds at the selected temperature. The peak hold involves applying a shear rate of 0.05 s$^{-1}$ at 20° C. for 3 min with sampling every 10 s. The continuous ramp step is performed at a shear rate from 0.1 to 1200 s$^{-1}$ for 3 min at 20° C. to obtain the full flow profile.

As described above, the composition may be a non-household care composition. For example, a non-household care composition can be selected from agricultural compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions, including cleaning and detergent compositions applicable to any such use while excluding fabric and household care compositions In one type of embodiment, the composition can include an agrochemical, e.g. one or more insecticides, fungicides, herbicides, pesticides, miticides, repellants, attractants, defoliaments, plant growth regulators, fertilizers, bactericides, micronutrients, and trace elements. Suitable agrochemicals and secondary agents are described in U.S. Pat. Nos. 6,204,223 and 4,681,228 and EP 0989803 A1. For example, suitable herbicides include paraquat salts (for example paraquat dichloride or paraquat bis(methylsulphate), diquat salts (for example diquat dibromide or diquat alginate), and glyphosate or a salt or ester thereof (such as glyphosate isopropylammonium, glyphosate sesquisodium or glyphosate trimesium, also known as sulfosate). Incompatible pairs of crop protection chemicals can be used in separate chambers, for example as described in U.S. Pat. No. 5,558,228. Incompatible pairs of crop protection chemicals that can be used include, for example, bensulfuron methyl and molinate; 2,4-D and thifensulfuron methyl;2,4-D and methyl 2-[[[[N-4-methoxy-6-methyl-1,3,5-triazine-2-yl)-N-methylamino]carbonyl]amino]-sulfonyl]benzoate; 2,4-D and metsulfuron methyl; maneb or mancozeb and benomyl; glyphosate and metsulfuron methyl; tralomethrin and any organophosphate such as monocrotophos or dimethoate; bromoxynil and N-[[4,6-dimethoxypyrimidine-2-yl)-amino]carbonyl]-3-(ethylsulfonyl)-2-pyridine-sulfonamide; bromoxynil and methyl 2-[[[[(4-methyl-6-methoxy)-1,3,5-triazin-2-yl)amino]carbonyl]amino]sulfonyl]-benzoate; bromoxynil and methyl 2-[[[[N-(4-methoxy-6-methyl-1,3,5-triazin-2-yl)-N-methylamino]carbonyl]amino]-sulfonyl] benzoate. In another, related, type of embodiment, the composition can include one or more seeds, optionally together with soil, and further optionally together with one or more additional components selected from mulch, sand, peat moss, water jelly crystals, and fertilizers, e.g. including types of embodiments described in U.S. Pat. No. 8,333,033.

In another type of embodiment, the composition is a water-treatment agent. Such agents include aggressive oxidizing chemicals, e.g. as described in U.S. Patent Application Publication No. 2014/0110301 and U.S. Pat. No. 8,728,593. For example, sanitizing agents can include hypochlorite salts such as sodium hypochlorite, calcium hypochlorite, and lithium hypochlorite; chlorinated isocyanurates such as dichloroisocyanuric acid (also referred to as "dichlor" or dichloro-s-triazinetrione, 1,3-dichloro-1,3,5-triazinane-2,4,6-trione) and trichloroisocyanuric acid (also referred to as "trichlor" or 1,3,5-trichloro-1,3,5-triazinane-2,4,6-trione). Salts and hydrates of the sanitizing compounds are also contemplated. For example, dichloroisocyanuric acid may be provided as sodium dichloroisocyanurate, sodium dichloroisocyanurate acid dihydrate, among others. Bromine containing sanitizing agents may also be suitable for use in unit dose packaging applications, such as 1,3-dibromo-5,5-dimethylhydantoin (DBDMH), 2,2-dibromo-3-nitrilopropionamide (DBNPA), dibromocyano acetic acid amide, 1-bromo-3-chloro-5,5-dimethylhydantoin; and 2-bromo-2-nitro-1,3-propanediol, among others. The oxidizing agent can be one described in U.S. Pat. No. 7,476,325, e.g. potassium hydrogen peroxymonosulfate. The composition can be a pH-adjusting chemical, e.g. as described in U.S. Patent Application Publication No. 2008/0185347, and can include, for example, an acidic component and an alkaline component such that the composition is effervescent when contacted with water, and adjusts the water pH. Suitable ingredients include sodium bicarbonate, sodium bisulfate, potassium hydroxide, sulfamic acid, organic carboxylic acids, sulfonic acids, and potassium dihydrogen phosphate. A buffer blend can include boric acid, sodium carbonate, glycolic acid, and oxone monopersulfate, for example.

A water-treatment agent can be or can include a flocculant, e.g. as described in U.S. Patent Application Publication No. 2014/0124454. The flocculant can include a polymer flocculant, e.g. polyacrylamide, a polyacrylamide copolymer such as an acrylamide copolymers of diallydimethylammonium chloride (DADMAC), dimethylaminoethylacrylate (DMAEA), dimethylaminoethylmethacrylate (DMAEM), 3-methylamidepropyltrimethylammonium chloride (MAPTAC) or acrylic acid; a cationic polyacrylamide; an anionic polyacrylamide; a neutral polyacrylamide; a polyamine; polyvinylamine; polyethylene imine; polydimethyldiallylammonium chloride; poly oxyethylene; polyvinyl alcohol; polyvinyl pyrrolidone; polyacrylic acid; polyphosphoric acid; polystyrene sulfonic acid; or any combination thereof. A flocculant can be selected from chitosan acetate, chitosan lactate, chitosan adipate, chitosan glutamate, chitosan succinate, chitosan malate, chitosan citrate, chitosan fumarate, chitosan hydrochloride, and combinations thereof. The water-treating composition can include a phosphate removing substance, e.g. one or more selected from a zirconium compound, a rare earth lanthanide salt, an aluminum compound, an iron compound, or any combination thereof.

The composition can be a limescale removing composition, e.g. citric or maleic acid or a sulphate salt thereof, or any mixture thereof, e.g. as described in U.S. Patent Application No. 2006/0172910.

Various other types of compositions are contemplated for use in the packets described herein, including particulates, for example down feathers, e.g. as described in US RE29059 E; super absorbent polymers, e.g. as described in U.S. Patent Application Publication Nos. 2004/0144682 and 2006/0173430; pigments and tinters, e.g. as described in U.S. Pat. No. 3,580,390 and U.S. Patent Application Publication No. 2011/0054111; brazing flux (e.g. alkali metal fluoroaluminates, alkali metal fluorosilicates and alkali metal fluorozincates), e.g. as described in U.S. Pat. No. 8,163,104; food items (e.g., coffee powder or dried soup) as described in U.S. Patent Application Publication No. 2007/0003719; and wound dressings, e.g. as described in U.S. Pat. No. 4,466,431.

Dissolution Chamber Residue Test

A water-soluble film characterized by or to be tested for undissolved residue according to the Dissolution Chamber (DC) Test is analyzed as follows using the following materials:

1. Beaker (4000 ml);
2. Stainless steel washers (3.5" (88.9 mm) OD, 1.875" ID (47.6 mm), 0.125" (3.18 mm) thick);
3. Styrene-butadiene rubber gaskets (3.375" (85.7 mm) OD, 1.91" ID (48.5 mm), 0.125" thick (3.18 mm));
4. Stainless steel screens (3.0" (76.2 mm) OD, 200×200 mesh, 0.0021" (0.053 mm) wire OD, 304SS stainless steel wire cloth);
5. Thermometer (0° C. to 100° C., accurate to +/−1° C.);
6. Cutting punch (1.5" (38.1 mm) diameter);
7. Timer (accurate to the nearest second);
8. Reverse osmosis (RO) water;
9. Binder clips (size #5 or equivalent);
10. Aluminum pans (2.0" (50.8 mm) OD); and
11. Sonicator.

For each film to be tested, three test specimens are cut from a selected test film having a thickness of 76 μm using the cutting punch. If cut from a film web made by a continuous process, the specimens should be cut from areas of web evenly spaced along the transverse direction of the web (i.e., perpendicular to the machine direction). Each test specimen is then analyzed using the following procedure:

1. Weigh the film specimen and track the specimen through the test. Record the initial film weight ($F_o$).
2. Weigh a set of two sonicated, clean, and dry screens for each specimen and track them through the test. Record the initial screen weights (collectively $S_o$ for the two screens combined).
3. Assemble a specimen dissolution chamber by flatly sandwiching the film specimen between the center of the two screens, followed by the two rubber gaskets (one gasket on each side between the screen and washer), and then the two washers.
4. Secure the dissolution chamber assembly with four binder clips evenly spaced around the washers and the clips folded back away from the screens.
5. Fill the beaker with 1,500 ml of RO water at laboratory room temperature (72+/−3° F., 22+/−2° C.) and record the room temperature.
6. Set the timer to a prescribed immersion time of 5 minutes.
7. Place the dissolution chamber assembly into the beaker and immediately start the timer, inserting the dissolution chamber assembly at an approximate 45 degree entry angle into the water surface. This entry angle helps remove air bubbles from the chamber. The dissolution chamber assembly rests on the beaker bottom such that the test specimen film is positioned horizontally about 10 mm from the bottom. The four folded-back binder clips of the dissolution chamber assembly are suitable to maintain the about 10 mm film clearance from the beaker bottom, however, any other equivalent support means may be used.
8. At the prescribed elapsed prescribed immersion time of 5 minutes, slowly remove the dissolution chamber assembly from the beaker at an approximate 45 degree angle.
9. Hold the dissolution chamber assembly horizontally over the aluminum pan to catch any drips from the screens and carefully remove the binder clips, washers, and gaskets. Do not break open the sandwiched screens.
10. Place the sandwiched screens (i.e., screen/residual undissolved film/screen) over the aluminum pan and into an oven at 100° C. for 30 minutes to dry.
11. Weigh the dried set of sandwiched screens including any residual undissolved film therein. Measure and add to this dried screen weight any dried film drippings captured in and recovered from (e.g., by scraping) the pan when the dissolution chamber assembly was first removed from the beaker and during drying. Record the final sandwiched screen weight (collectively $S_f$, including the dried film drippings).
12. Calculate % residue ("DC residue") left for the film specimen: % DC residue=$100*((S_f-S_o)/F_o)$.
13. Clean the sandwiched screens by soaking them in a beaker of RO water for about 20 minutes. Then, take them apart and do a final rinse in the sonicator (turned on and filled with RO water) for at least 5 minutes or until no residue is visible on the screens.

Suitable behavior of water-soluble films according to the disclosure is marked by films having about a 76 micron thickness having DC residue values of about 46 wt. % or less or about 48 wt. % or less, or about 50 wt. % or less, or about 52 wt. % or less as measured by the DC Test. Generally, lower DC residue values are desirable to reduce the likelihood of residual film remaining after use in aggressive conditions (e.g., in low water conditions and/or in cold water conditions). In various embodiments, the water-soluble film has a DC residue value of at least 1, 2, 5, 10, 12, 15, 25, 30, or 35 wt. % and/or up to about 15, 20, 30, 40, 45, 48, 50, or 52 wt. %; (e.g., about 5 wt. % to about 52 wt. %, or about 12 wt. % to about 50 wt. %, or about 25 wt. % to about 48 wt. %, or about 10 wt. % to about 46 wt. %, or about 20 wt. % to about 46 wt. %, or about 25 wt. % to about 46 wt. %).

Dissolution and Disintegration Test (MSTM 205)

A film can be characterized by or tested for Dissolution Time and Disintegration Time according to the MonoSol Test Method 205 (MSTM 205), a method known in the art. See, for example, U.S. Pat. No. 7,022,656.

Apparatus and Materials:
600 mL Beaker
Magnetic Stirrer (Labline Model No. 1250 or equivalent)
Magnetic Stirring Rod (5 cm)
Thermometer (0 to 100° C.±1° C.)
Template, Stainless Steel (3.8 cm×3.2 cm)
Timer (0-300 seconds, accurate to the nearest second)
Polaroid 35 mm slide Mount (or equivalent)
MonoSol 35 mm Slide Mount Holder (or equivalent)
Distilled water For each film to be tested, three test specimens are cut from a film sample using a template (i.e., 3.8 cm×3.2 cm specimen). If cut from a film web, specimens should be cut from areas of web evenly spaced along the traverse direction of the web. Each test specimen is then analyzed using the following procedure.

Lock each specimen in a separate 35 mm slide mount.

Fill beaker with 500 mL of distilled water. Measure water temperature with thermometer and, if necessary, heat or cool water to maintain temperature at 20° C. (about 68° F.).

Mark height of column of water. Place magnetic stirrer on base of holder. Place beaker on magnetic stirrer, add magnetic stirring rod to beaker, turn on stirrer, and adjust stir speed until a vortex develops which is approximately one-fifth the height of the water column. Mark depth of vortex.

Secure the 35 mm slide mount in the alligator clamp of the 35 mm slide mount holder such that the long end of the slide mount is parallel to the water surface. The depth adjuster of the holder should be set so that when dropped, the end of the clamp will be 0.6 cm below the surface of the water. One of the short sides of the slide mount should be next to the side of the beaker with the other positioned directly over the center of the stirring rod such that the film surface is perpendicular to the flow of the water.

In one motion, drop the secured slide and clamp into the water and start the timer. Disintegration occurs when the film breaks apart. When all visible film is released from the slide mount, raise the slide out of the water while continuing to monitor the solution for undissolved film fragments. Dissolution occurs when all film fragments are no longer visible and the solution becomes clear.

The results should include the following: complete sample identification; individual and average disintegration and dissolution times; and water temperature at which the samples were tested.

Film disintegration times (I) and film dissolution times (S) can be corrected to a standard or reference film thickness using the exponential algorithms shown below in Equation 1 and Equation 2, respectively.

$$I_{corrected} = I_{measured} \times (\text{reference thickness/measured thickness})^{2.0} \quad [1]$$

$$S_{corrected} = S_{measured} \times (\text{reference thickness/measured thickness})^{2.0} \quad [2]$$

Suitable behavior of water-soluble films according to the disclosure having a thickness of about 76 microns is marked by dissolution times of 300 seconds or less, or about 250 seconds or less, or about 200 seconds or less, or about 150 seconds or less, or about 100 seconds or less, or about 90 seconds or less, or about 80 seconds or less, or about 70 seconds or less as measured by MSTM-205.

In general, the solubility of a water soluble film is inversely related to the molecular weight of the water soluble resin and the crystallinity of the water soluble resin. Accordingly, a film comprising a high molecular weight PVOH resin can have adequate solubility if the resin has a lower degree of hydrolysis (i.e., more residual acetate groups), for example, in the range of about 75 to 93, about 80 to 93, about 84 to 93, about 85 to 93, or about 87 to 93, and/or includes a comonomer which provides a non-hydrolyzable pendant group that can interrupt the ordered alignment of the polymer chains. One of ordinary skill in the art will also recognize that for a specific molecular weight of the water soluble resin that the formulated fill will become more soluble with increasing plasticizer levels and less soluble with decreasing plasticizer levels.

Tensile Strength Test and Modulus Test

A water-soluble film characterized by or to be tested for tensile strength according to the Tensile Strength (TS) Test and modulus (or tensile stress) according to the Modulus (MOD) Test is analyzed as follows. The procedure includes the determination of tensile strength and the determination of modulus at 10% elongation according to ASTM D 882 ("Standard Test Method for Tensile Properties of Thin Plastic Sheeting") or equivalent. An INSTRON tensile testing apparatus (Model 5544 Tensile Tester or equivalent) is used for the collection of film data. A minimum of three test specimens, each cut with reliable cutting tools to ensure dimensional stability and reproducibility, are tested in the machine direction (MD) (where applicable) for each measurement. Tests are conducted in the standard laboratory atmosphere of 23±2.0° C. and 35±5% relative humidity. For tensile strength or modulus determination, 1"-wide (2.54 cm) samples of a single film sheet having a thickness of 75 µm are prepared. The sample is then transferred to the INSTRON tensile testing machine to proceed with testing while minimizing exposure in the 35% relative humidity environment. The tensile testing machine is prepared according to manufacturer instructions, equipped with a 500 N load cell, and calibrated. The correct grips and faces are fitted (INSTRON grips having model number 2702-032 faces, which are rubber coated and 25 mm wide, or equivalent). The samples are mounted into the tensile testing machine and analyzed to determine the 100% modulus (i.e., stress required to achieve 100% film elongation) and tensile strength (i.e., stress required to break film).

Suitable behavior of water-soluble films according to the disclosure is marked by TS values of at least about 27 MPa as measured by the TS Test at 35% RH. Generally, higher TS values are desirable because they correspond to stronger pouch seals when the film is the limiting or weakest element of a seal. In various embodiments, the water-soluble film has a TS value of at least about 27, 28, 29, 30, 31, 32, 33, 34, 35, or 36 MPa and/or up to about 35, 38, 40, 45, or 50 MPa (e.g., about 27 MPa to about 48 MPa or about 30 MPa to about 38 MPa). Alternatively or additionally, an upper bound for a suitable TS value range can be a TS value for a corresponding water-soluble film having only a single PVOH polymer or PVOH copolymer of the PVOH polymers and PVOH copolymers in the PVOH resin blend (e.g., a corresponding single-resin film having the higher TS value).

Suitable behavior of water-soluble films according to the disclosure is marked by MOD values of at least about 20 N/mm$^2$ as measured by the MOD Test at 35% RH. Generally, higher MOD values are desirable because they correspond to pouches having a greater stiffness and a lower likelihood of deforming and sticking to each other when loaded on top of each other during production or in final consumer packaging. Further, MOD values at 10% elongation correspond to the ability of the film to maintain stiffness rather than loosen and droop when in contact with liquid pouch contents. In particular, films having higher MOD values correspond to pouches that are less likely to soften and take on a loose and droopy appearance when in contact with liquid pouch contents comprising a low molecular weight polyol. In various embodiments, the water-soluble film has a MOD value of at least about 20, 21, 22, 23, 24, 25, or 27 N/mm$^2$ and/or up to about 24, 25, 27, 28, 29, or 30 N/mm$^2$ (e.g., about 20 N/mm$^2$ to about 30 N/mm$^2$, or about 20 N/mm$^2$ to about 28 N/mm$^2$, or about 22 N/mm$^2$ to about 25 N/mm$^2$). Alternatively or additionally, an upper bound for a suitable MOD value range can be a MOD value for a corresponding water-soluble film having only a single PVOH polymer or PVOH copolymer of the PVOH polymers and PVOH copolymers in the PVOH resin blend (e.g., a corresponding single-resin film having the higher MOD value).

Liquid Release Test

A water-soluble film and/or pouch characterized by or to be tested for delayed solubility according to the Liquid Release Test is analyzed as follows using the following materials:

2 L beaker and 1.2 liters of deionized (DI) water
Water soluble pouch to be tested; the film has a thickness of 88 µm; the pouch is pre-conditioned for two weeks at 38° C.
Thermometer
Wire cage
Timer Before running the experiment, ensure that enough DI water is available to repeat the experiment five times, and ensure that the wire cage and beaker are clean and dry.

The wire frame cage is a plastic coated wire cage (4"× 3.5"×2.5") with no sharp edges, or equivalent. The gauge of the wire should be about 1.25 mm and the wire should have openings the size of 0.5 inch (1.27 cm) squares. An example image of a cage 28 with test pouches 30 is shown in FIG. 1.

To set up for the test, carefully place the water soluble pouch in the cage while not scratching the pouch on the cage and allowing free space for the pouch to move. Do not bind the pouch tightly with the wire cage, while still ensuring it is secure and will not come out of the cage. The orientation of the pouch in the cage should be such that the natural buoyancy of the pouch, if any, is allowed (i.e. the side of the pouch that will float to the top should be placed towards the top). If the pouch is symmetrical, the orientation of the pouch generally would not matter.

Next, fill the 2 L beaker with 1200 milliliters of 20° C. DI water.

Figure 2:
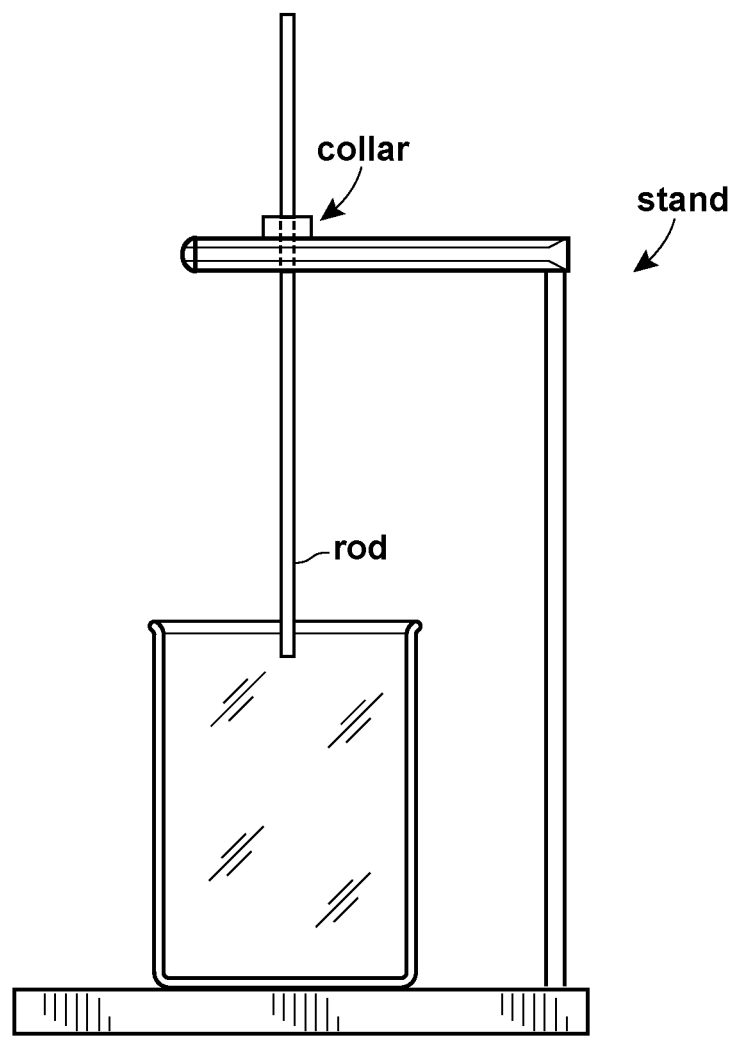
FIG. 2 shows an apparatus for performing the Liquid Release Test, including a beaker resting on a stand, the stand holding a rod for lowering a cage into the beaker, the rod being fixable by a collar with a set screw (not shown).

Next, lower the wire frame cage with the enclosed pouch into the water. Ensure that the cage is 1 inch (2.54 cm) from the bottom of the beaker. Be sure to fully submerge the pouch on all sides. Ensure that the cage is stable and will not move and start a timer as soon as the pouch is lowered into the water. The position of the cage with respect to the water in the beaker can be adjusted and maintained by any suitable means, for example by using a clamp fixed above the beaker, and a rod attached to the top of the cage. The clamp can engage the rod to fix the position of the cage, and tension on the clamp can be lowered in order to lower the cage into the water. Other means of frictional engagement can be used in the alternative to a clamp, for example a collar with a set screw, as shown in FIG. 2 (set screw not shown). FIG. 2 shows a beaker 30 resting on a stand 40, the stand holding a rod 50 for lowering a cage 10 (not shown) into the beaker 30, the rod 50 being able to hold a fixed vertical position by use of a collar 60 having a set screw (not shown) that engages the rod 50, for example by friction or by engagement with a hole (not shown) in the rod 50.

Liquid content release is defined as the first visual evidence of the liquid leaving the submerged pouch.

Use the timer to record when the liquid content is released in to the surrounding water (Release Time) with a stopping point of 45 seconds.

A pass or fail grade will be given to each pouch. A pass grade is received if the soluble pouch retained its liquid for 30 seconds or longer. A fail grade is received if the soluble pouch did not retain its liquid for at least 30 seconds.

Repeat this process with new DI water and a new water soluble pouch five times for each film being tested.

A total of 5 pouches are tested for each film sample type unless reported otherwise.

Compression Test Measurement—Pouch Strength Test

A water-soluble film and/or pouch characterized by or to be tested for the ability of a water soluble capsule to resist a mechanical compression strength of a minimum of 200 N at 60% RH according to the Pouch Strength Test is analyzed as follows using the following materials:

Instron Model 5544 (or equivalent)
Water-soluble pouch or capsule to be tested the film has a thickness of 76 μm; the pouch is pre-conditioned for at least 24 hours at 23±1° C. ad 60±4% Relative Humidity.
Zipper type bags
Two flat plates (Top plate: 10 KN Max load T1223-1022/ Bottom plate: 100KN Max load T489-74)
Load cell (Static load±2 kN, Max spindle torque 20 Nm, bolt torque 25 Nm, and weight 1.2 kg)
Marker
Allen wrench (6 mm)

The pouch is inspected for leaks and then placed into a zippered bag (approximately 57 micron thick on each side). Seal the bag with minimal air inside. Label the bag with the sample name and number.

Open the method for compression test. Ramp speed should be 4 mm/s.

Carefully place the sample, cavity side down, between the two plates making sure the pouch is on the center of the bottom plate. Move capsule inside the bag away from any edges.

Press start to run the test. As the two plates come together, the pouch will burst. Record the compression strength and the location on the pouch where the rupture occurred. Repeat this process for all samples.

Suitable behavior of water-soluble films according to the disclosure is marked by compression values of at least about 200 N and less than about 2000N as measured by the Pouch Strength Test. In embodiments, the outer wall film is characterized by a pouch strength of at least about 200 N when formed into a single compartment pouch, sealed, conditioned, and tested according to the Pouch Strength Test. In embodiments, the water soluble pouch comprising outer wall films and inner wall film, wherein the outer wall films are sealed to the inner wall film is characterized by a pouch strength of at least about 200 N.

In general, the pouch strength of a water soluble film is related to the molecular weight of the water soluble resin and the crystallinity of the water soluble resin. Accordingly, a film comprising a low molecular weight PVOH resin can have adequate strength if the resin has a higher degree of hydrolysis (i.e., fewer residual acetate groups), and/or includes little to no comonomer having a non-hydrolyzable pendant group that can interrupt the ordered alignment of the polymer chains. One of ordinary skill in the art will also recognize that for a specific molecular weight of the water soluble resin that the formulated film will have lower strength with increasing plasticizer levels and higher strength with decreasing plasticizer levels.

Tackinsess PA Test

A water-soluble film characterized by or to be tested for adhesion (or tackiness) according to the Tackiness Peak Area (PA) Test is analyzed as follows. The tackiness test value is the positive area under the curve of a tackiness (adhesion) test. The positive area is similar to or equivalent to work of adhesion. Films are tested within 8 weeks of forming. Films are stored under ambient condition until tested. The tackiness of an aged film can also be determined and is referred to as the Aged Adhesion (AA or 2W-PA) value. For aging, a film sample capable to produce a minimum of three test specimens is first conditioned by being placed in a foil laminate pouch with minimal head space and heat sealed closed. The pouch is placed in 35° C. oven for 14 days. After the 14 days, the pouch is removed and allowed to cool to room temperature. A higher tackiness and/or AA value is favorable and is representative of seal strength.

The test is performed using a Stable Microsystems (XT+ specification) texture analyzer or equivalent fitted with a pasta firmness rig and an overhead probe spray gun (BADGER 200-3 or equivalent) for water application. The test is performed with the following standard tackiness method parameters: Coat Weight 0.02 g, Open Time 5 sec, Sealing Force 50 kg, Sealing Time 0.15 sec, and Curing Time 10 sec. Samples are prepared under controlled conditions (21° C., 35% RH) by cutting two film pieces of 14 cm×9 cm and then, using double-sided tape, fixing one layer to the pasta firmness rig (lower platform) and one layer to the upper probe by carefully smoothing out any potential wrinkle. Three specimen replicates are then tested according to the following procedure:

1. Position the spray gun at 20.5 cm above the lower platform;
2. Spray water in order to apply 0.02 g at the center of the lower film layer;
3. Bring upper probe down until combining film layers and apply 50 kg pressure for 0.15 s, with the time between water application and combining being set at 5 s;
4. Release pressure and maintain contact for 10 s (force for relaxation at 100 g);
5. Bring upper probe back-up at a constant speed of 12 mm/s; and
6. Record 'positive area' as the work of adhesion of the film specimen.

Suitable behavior of water-soluble films according to the disclosure is marked by tackiness values of fresh samples of at least about 1500, 1800, or 2000 g/s and/or up to about 3000, 4500, 6000, 8000, 10,000, 15,000, or 20,000 g/s.

Above the lower threshold levels (e.g., within a range also defined by an upper bound), the films exhibit improved seal strength. Accordingly, in embodiments, the inner film has a tackiness value of at least 1500 as measured by the Tackiness PA Test.

In general, the tackiness of a water soluble film, and therefore, the sealability, is inversely related to the molecular weight of the water soluble resin. Accordingly, a lower molecular weight PVOH resin, for example having a viscosity in the range of about 12 to about 14.5 cP, can provide a film having an acceptable tackiness value. Further, the tackiness is inversely related to the degree of hydrolysis and crystallinity of the PVOH resin.

Leaker Test

Pouches enclosing liquid compositions were visually inspected for leaking. 200 pouches were formed for each example, using 16 g/m² sealing solution to form sealed compartments (unless noted otherwise). Pouches are filled with liquid to about 80% of the internal volume. The results of the visual inspection are recorded as the raw number of pouches with visible leaking.

The water soluble films and pouches in accordance with the disclosure can be better understood in light of the following examples, which are merely intended to illustrate the water soluble films and are not meant to limit the scope thereof in any way.

Specifically contemplated embodiments of the disclosure are herein described in the following numbered paragraphs. These embodiments are intended to be illustrative in nature and not intended to be limiting.

1. A water soluble pouch comprising at least two sealed compartments, the pouch comprising
   outer walls comprising water soluble film comprising a water soluble resin;
   and an inner wall comprising water soluble film comprising a water soluble resin;
   the outer wall films being sealed to the inner wall film;
      the outer wall films being characterized by
         a dissolution time of 300 seconds or less in water at a temperature of 20° C. for an outer wall film having a thickness of about 76 micron in accordance with MonoSol Test Method MSTM-205;
         the water soluble resin of the outer wall films having a 4% solution viscosity at 20° C. in a range of 14.5 cP to 25 cP; and
         a pouch strength of at least 200 N as measured by the outer wall film sealed and tested according to the Pouch Strength Test; and
      the inner wall film being characterized by:
         a dissolution time of 300 seconds or less in water at a temperature of 20° C. for an inner wall film having a thickness of about 76 micron in accordance with MonoSol Test Method MSTM-205;
         the water soluble resin of the inner film having a 4% solution viscosity at 20° C. in a range of 12 cP to 14.5 cP; and
         a tackiness value of at least 1500 g/s for an inner film tested according to the Tackiness PA Test.

2. The water soluble pouch of paragraph 1, wherein the water soluble resin of the outer wall film comprises a polyvinyl alcohol or copolymer thereof.

3. The water soluble pouch of paragraph 1 or paragraph 2, wherein the water soluble resin of the inner wall film comprises a polyvinyl alcohol or a copolymer thereof.

4. The water soluble pouch of any one of paragraphs 1 to 3, wherein the water soluble resin of the outer wall film comprises a blend of a polyvinyl alcohol homopolymer and a polyvinyl alcohol copolymer comprising an anionic monomer unit.

5. The water soluble pouch of paragraph 4, wherein blend comprises from 30 to 100 weight percent of the polyvinyl alcohol copolymer comprising an anionic monomer unit and from 0 to 70 weight percent of the polyvinyl alcohol homopolymer, based on the total weight of polyvinyl alcohol in the film.

6. The water soluble pouch of paragraph 5, wherein the blend comprises from 30 to 70 weight percent, or from 30 to 65 weight percent, or from 30 to 50 weight percent of the polyvinyl alcohol copolymer comprising an anionic monomer unit, based on the total weight of polyvinyl alcohol in the film.

7. The water soluble pouch of any one of paragraphs 1 to 6, wherein the water soluble resin of the inner wall film comprise a blend of one or more polyvinyl alcohol homopolymers and a polyvinyl alcohol copolymer comprising an anionic monomer unit.

8. The water soluble pouch of paragraph 7, wherein blend comprises from 30 to 100 weight percent of the polyvinyl alcohol copolymer comprising an anionic monomer unit and from 0 to 70 weight percent of the one or more polyvinyl alcohol homopolymers, based on the total weight of polyvinyl alcohol in the film.

9. The water soluble pouch of paragraph 8, wherein the blend comprises from 30 to 70 weight percent, or from 30 to 65 weight percent, or from 30 to 50 weight percent of the polyvinyl alcohol copolymer comprising an anionic monomer unit, based on the total weight of polyvinyl alcohol in the film.

10. The water soluble pouch of any one of paragraphs 4 to 9, wherein the anionic monomer unit is selected from the group consisting of vinyl acetic acid, alkyl acrylates, maleic acid, monoalkyl maleate, dialkyl maleate, monomethyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts of the foregoing, esters of the foregoing, and combinations of the foregoing.

11. The water soluble pouch of paragraph 10, wherein the anionic monomer unit comprises one or more of maleic acid, monoalkyl maleate, dialkyl maleate, monomethyl maleate, dimethyl maleate, maleic anhydride, alkali metal salts of the foregoing and combinations thereof.

12. The water soluble pouch of paragraph 11, wherein the maleic acid is selected from the group consisting of maleic acid, monomethyl maleate, dimethyl maleate, maleic anhydride, alkali metal salts of the foregoing, esters of the foregoing, and combinations thereof.

13. The water soluble pouch of any one of paragraphs 4 to 12, wherein the polyvinyl alcohol copolymer comprises from 2 to 8 mol % of the anionic monomer unit, or 1 to 4 mol % of the anionic monomer unit.

14. The water soluble pouch of any of paragraphs 2 to 13, wherein the water soluble resin of the outer wall film comprises a degree of hydrolysis in a range of 87 to 93, or if a blend of polyvinyl alcohol resins is used then the arithmetic weight average degree of hydrolysis is in a range of 87 to 93.

15. The water soluble pouch of any of paragraphs 3 to 14, wherein the water soluble resin of the inner wall film comprises a degree of hydrolysis in a range of 87 to 93, or if a blend of polyvinyl alcohol resins is used then the arithmetic weight average degree of hydrolysis is in a range of 87 to 93.

16. The water soluble pouch of any of paragraphs 1 to 15, wherein the water soluble resin, or resin blend, of the outer wall films has a 4% solution viscosity at 20° C. in a range of 14.5 cP to 21 cP.

17. The water soluble pouch of paragraph 16, wherein the water soluble resin, or resin blend, of the outer wall films has a 4% solution viscosity at 20° C. in a range of 15.5 cP to 20 cP.

18. The water soluble pouch of any one of paragraphs 1 to 17, wherein the outer wall films each are characterized by a pouch strength of less than 2000 N as measured by the outer wall film sealed, conditioned, and tested according to the Pouch Strength Test.

19. The water soluble pouch of any one of paragraphs 1 to 18, wherein the pouch has a pouch strength of at least 200 N as measured by the Pouch Strength Test.

20. The water soluble pouch of any one of paragraphs 1 to 19, wherein the inner wall film has a thickness of at least 75 micron.

21. The water soluble pouch of any one of paragraphs 1 to 20, wherein the outer wall films further comprise a plasticizer.

22. The water soluble pouch of any one of paragraphs 1 to 21, wherein the inner wall film further comprises a plasticizer.

23. The water soluble pouch of paragraph 21 or paragraph 22, wherein the plasticizer is selected from the group consisting of glycerin, trimethylol propane, sorbitol, and combinations thereof.

24. The water soluble pouch of any one of paragraphs 1 to 23, wherein the outer wall films further comprise a surfactant.

25. The water soluble pouch of any one of paragraphs 1 to 24, wherein the inner wall film further comprises a surfactant.

26. The water soluble pouch of paragraph 24 or paragraph 25, wherein the surfactant is selected from the group consisting of polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, and amine oxides, N-alkylbetaines, sulfobetaines, and combinations thereof.

27. The water soluble pouch of any one of paragraphs 1 to 25, wherein the outer wall films further comprise an aversive agent.

28. The water soluble pouch of any one of paragraphs 1 to 27, wherein the inner wall films further comprise an aversive agent.

29. The water soluble pouch of any one of paragraphs 1 to 28, wherein the thickness of each of the outer wall films does not vary from the thickness of the inner wall film by more than 10% for non-thermoformed films.

30. The water soluble pouch of any one of paragraphs 1 to 29, wherein a composition is enclosed in the pouch.

31. The water soluble pouch of paragraph 30, wherein the composition is a liquid.

32. The water soluble pouch of paragraph 31, wherein the liquid composition comprises a composition selected from the group consisting of agricultural compositions, aviation compositions, food and nutritive compositions, industrial compositions, livestock compositions, marine compositions, medical compositions, mercantile compositions, military and quasi-military compositions, office compositions, and recreational and park compositions, pet compositions, water-treatment compositions, and combinations thereof.

33. The water soluble pouch of any one of paragraphs 1 to 32, wherein the outer wall water soluble resin is not the same as the inner wall water soluble resin.

34. A water soluble pouch comprising
at least two outer walls comprising water soluble film comprising a water soluble resin;
and at least one inner wall comprising water soluble film comprising a water soluble resin; the at least one inner wall having a first side and a second side and a thickness therebetween;
the at least two outer wall films being sealed to the at least one inner wall film to form a compartment; wherein the at least two outer wall films are not sealed to the same side of the at least one inner wall such that at least two compartments are formed;
the outer wall films being characterized by
a dissolution time of 300 seconds or less in water at a temperature of 20° C. for an outer wall film having a thickness of about 76 micron in accordance with MonoSol Test Method MSTM-205;
the water soluble resin of the outer wall films having a 4% solution viscosity at 20° C. in a range of 14.5 cP to 25 cP; and
a pouch strength of at least 200 N as measured by the outer wall film sealed and tested according to the Pouch Strength Test; and
the inner wall film being characterized by:
a dissolution time of 300 seconds or less in water at a temperature of 20° C. for an inner wall film having a thickness of about 76 micron in accordance with MonoSol Test Method MSTM-205;
the water soluble resin of the inner film having a 4% solution viscosity at 20° C. in a range of 12 cP to 14.5 cP; and
a tackiness value of at least 1500 g/s for an inner film tested according to the Tackiness PA Test.

35. A water soluble pouch defining an interior pouch volume, the pouch comprising at least two water-soluble films, wherein a film of the at least two water-soluble films comprises a polyvinyl alcohol resin comprising a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing, and wherein the water-soluble film comprising a polyvinyl alcohol copolymer comprising an anionic monomer unit is sealed to another film using a sealing solution comprising water, one or more diols and/or glycols, and a surfactant.

36. The water-soluble pouch of paragraph 35, wherein the surfactant is one or more selected from polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), amine oxides, N-alkylbetaines and sulfobetaines (zwitterionics), dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids, 37. The water-soluble pouch of paragraph 36, wherein the surfactant is one or more selected from polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, amine oxides, N-alkylbetaines, sulfobetaines, and combinations thereof.

38. The water-soluble pouch of paragraph 35, wherein both films comprise a polyvinyl alcohol resin comprising a polyvinyl alcohol copolymer comprising an anionic monomer unit, optionally one or more of maleic acid, monoalkyl maleate, dialkyl maleate monomethyl maleate dimethyl maleate, maleic anhydride, alkali metal salts of the foregoing, esters of the foregoing, and combinations of the foregoing.

39. The pouch of any one of the preceding paragraphs 35-38, wherein one or both copolymer-containing polyvinyl alcohol resins have a 4% solution viscosity at 20° C. in a range of 12 cP to 25 cP.

40. The pouch of paragraph 39, wherein the resin has a 4% solution viscosity at 20° C. in a range of 14.5 cP to 25 cP 41. The pouch of any one of the preceding paragraphs 35-40, wherein one or both of the films is a blend of the copolymer resin further comprising a polyvinyl alcohol homopolymer resin.

42. The pouch of paragraph 41, wherein the blend in one or both films comprises from 30 to 100 weight percent of the polyvinyl alcohol copolymer comprising an anionic monomer unit and from 0 to 70 weight percent of the polyvinyl alcohol homopolymer, based on the total weight of polyvinyl alcohol in the film.

43. The pouch of any one of the preceding paragraphs 35-42, wherein the anionic monomer unit in one or both films is selected from the group consisting of vinyl acetic acid, alkyl acrylates, maleic acid, monoalkyl maleate, dialkyl maleate, monomethyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts of the foregoing, esters of the foregoing, and combinations of the foregoing.

44. The pouch of paragraph 43, wherein the anionic monomer unit in one or both films comprises one or more of maleic acid, monoalkyl maleate, dialkyl maleate, monomethyl maleate, dimethyl maleate, maleic anhydride, alkali metal salts of the foregoing and combinations thereof.

45. The pouch of paragraph 44, wherein the anionic monomer unit in one or both films is selected from the group consisting of maleic acid, monomethyl maleate, dimethyl maleate, maleic anhydride, alkali metal salts of the foregoing, esters of the foregoing, and combinations thereof.

46. The pouch of paragraph 45, wherein the wherein the blend in one or both films comprises at least 65 weight percent of the polyvinyl alcohol copolymer comprising an anionic monomer based on the total weight of polyvinyl alcohol in the film.

47. The pouch of any one of the preceding paragraphs 35-46, wherein the polyvinyl alcohol copolymer in one or both films comprises from 2 to 8 mol % of the anionic monomer unit, or 1 to 4 mol % of the anionic monomer unit.

48. The pouch of any one of the preceding paragraphs 35-47, wherein the water soluble resin has a degree of hydrolysis in a range of 87 to 93, or if a blend of polyvinyl alcohol resins is used then the arithmetic weight average degree of hydrolysis is in a range of 87 to 93.

49. The pouch of any one of the preceding paragraphs 35-48, wherein one or both anionic copolymer films is characterized by a pouch strength of less than 2000 N as measured by the film sealed, conditioned, and tested according to the Pouch Strength Test.

50. The pouch of any one of the preceding paragraphs 35-49, wherein the pouch has a pouch strength of at least 200 N as measured by the Pouch Strength Test.

51. The pouch of any one of the preceding paragraphs, wherein one or both copolymer-containing films further comprise a plasticizer.

52. The pouch of paragraph 51, wherein the plasticizer is selected from the group consisting of glycerin, trimethylol propane, sorbitol, and combinations thereof.

53. The pouch of any one of the preceding paragraphs 35-52, wherein one or both copolymer-containing films further comprise a surfactant.

54. The pouch of paragraph 53, wherein the surfactant is selected from the group consisting of polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, and amine oxides, N-alkylbetaines, sulfobetaines, and combinations thereof.

55. The pouch of any one of the preceding paragraphs 35-65, wherein at least one film further comprises an aversive agent.

56. The pouch of any one of the preceding paragraphs 35-55, wherein one or both copolymer-containing film has a tackiness value of at least 1500 g/s for the film tested according to the Tackiness PA Test.

57. A method of making a water-soluble pouch according to any one of the preceding paragraphs 35-56, comprising solvent sealing the two water-soluble films to each other with a sealing solution comprising water, one or more diols and/or glycols, and a surfactant.

EXAMPLES

Example 1

A water soluble film including a blend of a PVOH homopolymer and a PVOH copolymer comprising an anionic monomer unit was prepared. The PVOH homopolymer and PVOH copolymer are described in Table 1, below.

TABLE 1

| | PVOH homopolymer | PVOH copolymer | Blend |
|---|---|---|---|
| Weight percent, based on total PVOH in blend | 60% | 40% | 100% |

TABLE 1-continued

|  | PVOH homopolymer | PVOH copolymer | Blend |
|---|---|---|---|
| Anionic modification (mol %) | — | Maleate modified (4 mol %) | — |
| Viscosity (cP) | 21.8 | 16 | 19.3 |
| Degree of Hydrolysis | 87.4 | 89.1 | 88.1 |

The film formulation further included about 42 phr plasticizers, about 7 phr surfactants, and minor amounts of processing aids e.g., filler, antifoam, antiblock, bleaching agents, and aversive agents in an amount totaling less than about 9 phr.

Water soluble film having a thickness of about 75 microns was prepared. The film was tested for dissolution time according to MonoSol Test Method MSTM-205 and for tackiness value according to the Tackiness Test, described above. Pouches were prepared from the film of Example 1 using a coat weight of 16 g/m² of a sealing solution to seal the films together. The pouches were tested according to the Pouch Strength Test and Leaker Test, described above. The results are shown in Table 2, below.

TABLE 2

|  | Dissolution time | Tackiness value | Pouch Strength | Leaker | DC Residue (%) |
|---|---|---|---|---|---|
| Example 1 | <300 seconds | 1800 g/s | 355 N | 80 of 200 pouches leaked | 46 |

The film of Example 1 included a resin blend having a log average viscosity in a range of 14.5 cP to 25 cP and demonstrated acceptable dissolution, a DC residue of 46%, and the pouches made therefrom demonstrated a pouch strength of greater than 200 N. Thus, Example 1 demonstrates an outer film according to the disclosure. However, the pouches made of the film of Example 1 demonstrated unacceptable leaking, indicating poor sealability.

Example 2

A water soluble film including a blend of a PVOH homopolymer and a PVOH copolymer comprising an anionic monomer unit was prepared. The PVOH homopolymer and PVOH copolymer are described in Table 3, below.

TABLE 3

|  | PVOH homopolymer | PVOH copolymer | Blend |
|---|---|---|---|
| Weight percent, based on total PVOH in blend | 70% | 30% | 100% |
| Anionic modification (mol %) | — | Maleate modified (4 mol %) | — |
| Viscosity (cP) | 11.8 | 16 | 12.9 |
| Degree of Hydrolysis | 87.9 | 89.1 | 88.3 |

The film formulation further included about 40 phr plasticizers, about 6.5 phr surfactants, and minor amounts of processing aids e.g., filler, antifoam, antiblock, and bleaching agents in an amount totaling less than about 6.5 phr.

Films and pouches were prepared as in Example 1. The film of Example 2 was tested for dissolution time according to MonoSol Test Method MSTM-205 and for tackiness value according to the Tackiness Test, described above. The pouches of Example 2 were tested according to the Pouch Strength Test and Leaker Test, described above. The results are shown in Table 4, below.

TABLE 4

|  | Dissolution time | Tackiness value | Pouch Strength | Leaker | DC Residue |
|---|---|---|---|---|---|
| Example 2 | <300 seconds | 2250 g/s | 224 N | 0 of 200 pouches leaked | 48% |

The film of Example 2 included a resin blend having a log average viscosity in the range of 12 cP to 14.5 cP and demonstrated acceptable dissolution, had a DC Residue of 48%, and had a tackiness value greater than 1500 g/s. Thus, Example 2 demonstrates an inner film according to the disclosure with improved sealing properties. However, the pouch strength of Example 2 is considered low.

Example 3

Water soluble pouches having an inner film and outer films as described in Table 5, below, were prepared. The inner and outer films each further included about 40-42 phr plasticizers, about 6.5-7 phr surfactants, and minor amounts of processing aids e.g., filler, antifoam, antiblock, and bleaching agents in an amount totaling less than about 6.5-9 phr.

TABLE 5

|  | PVOH homopolymer | PVOH copolymer | Blend |
|---|---|---|---|
| Outer Film |  |  |  |
| Weight percent, based on total PVOH in blend | 60% | 40% | 100% |
| Anionic modification (mol %) | — | Maleate modified (4 mol %) | — |
| Viscosity (cP) | 21.8 | 16 | 19.3 |
| Degree of Hydrolysis | 87.4 | 89.1 | 88.1 |
| Inner Film |  |  |  |
| Weight percent, based on total PVOH in blend | 70% | 30% | 100% |
| Anionic modification (mol %) | — | Maleate modified (4 mol %) | — |
| Viscosity (cP) | 11.8 | 16 | 12.9 |
| Degree of Hydrolysis | 87.9 | 89.1 | 88.3 |

Films were prepared according to Example 1. Pouches were prepared from the films of Example 3 using a coat weight of 16 g/m² of a sealing solution to seal the films together. The pouches were formed with a top outer film, an inner film and a bottom outer film, each film approximating a rectangle in shape, with the films in a layered orientation and sealed at the periphery of the films. The top outer film was sealed to a first side of the inner film creating a defined first internal volume that contained a liquid described above. The bottom outer film was sealed to a second side of the inner film creating a defined second internal volume that contained a liquid described above. The pouches were tested according to the Pouch Strength Test and Leaker Test, described above. The results are shown in Table 6, below.

TABLE 6

| | Pouch Strength | Leaker |
|---|---|---|
| Example 3 | 320 N | 0 of 200 pouches leaked |

Thus, Example 3 demonstrates a two compartment pouch of the disclosure comprising outer wall film of the disclosure and inner wall film of the disclosure.

Example 4

Water soluble pouches having single compartments were prepared from the films of Examples 1 and 2, and multi-compartment pouches were prepared having the inner and outer films of Example 3. The pouches were prepared as in Example 1, except the coat weight was varied. The pouches were tested according to the Leaker Test, described above. The results are shown in Table 7, below.

TABLE 7

| | 13 g/m$^2$ | 16 g/m$^2$ | 19 g/m$^2$ |
|---|---|---|---|
| Pouch of Example 1 | 70 of 200 pouches leaked | 80 of 200 pouches leaked | 100 of 200 pouches leaked |
| Pouch of Example 2 | 0 of 200 pouches leaked | 0 of 200 pouches leaked | 0 of 200 pouches leaked |
| Pouch of Example 3 | 0 of 200 pouches leaked | 0 of 200 pouches leaked | 1 of 200 pouches leaked |

Thus, Example 4 demonstrate that multi-compartment pouches according to the disclosure demonstrate improved resistance to leaking compared to pouches prepared from the outer wall film and can be prepared such that the coat weight window is at least 6 g/m$^2$.

Example 5

Water soluble pouches having an inner film and outer films as described in Table 8, below, were prepared. The inner and outer films each further included about 38-40 phr plasticizers, about 7 phr surfactants, and minor amounts of processing aids e.g., filler, antifoam, antiblock, and bleaching agents in an amount totaling less than about 9 phr.

TABLE 8

| | PVOH homopolymer | PVOH copolymer | Blend |
|---|---|---|---|
| Outer Film | | | |
| Weight percent, based on total PVOH in blend | 70% | 30% | 100% |
| Anionic modification (mol %) | — | Maleate modified (4 mol %) | — |
| Viscosity (cP) | 17.2 | 16 | 16.8 |
| Degree of Hydrolysis | 87.6 | 89.1 | 88.1 |
| Inner Film | | | |
| Weight percent, based on total PVOH in blend | 70% | 30% | 100% |
| Anionic modification (mol %) | — | Maleate modified (4 mol %) | — |
| Viscosity (cP) | 11.8 | 16 | 12.9 |
| Degree of Hydrolysis | 87.9 | 89.1 | 88.3 |

Films and pouches were prepared according to Example 1. The outer film of Example 5, when formed into a single compartment pouch, sealed, conditioned, and tested according to the Pouch Strength Test, had a pouch strength of 379 N. The outer wall film further had a DC Residue value of 52. The multi-component pouches of Example 5 were tested according to the Pouch Strength Test and Leaker Test, described above. The results are shown in Table 9, below.

TABLE 9

| | Pouch Strength | Leaker |
|---|---|---|
| Example 3 | 337 N | 0 of 200 pouches leaked |

Thus, Example 5 demonstrates a two compartment pouch of the disclosure.

Example 6

Water soluble pouches having an inner film and outer films as described in Table 10, below, were prepared. The inner and outer films each further included about 38 phr plasticizers, about 6-7 phr surfactants, and minor amounts of processing aids e.g., filler, antifoam, bittering agents, antiblock, and bleaching agents in an amount totaling less than about 6-7 phr.

TABLE 10

| | PVOH homopolymer | PVOH copolymer | Blend |
|---|---|---|---|
| Outer Film | | | |
| Weight percent, based on total PVOH in blend | 70% | 30% | 100% |
| Anionic modification (mol %) | — | Maleate modified (4 mol %) | — |
| Viscosity (cP) | 17.2 | 16 | 16.7 |
| Degree of Hydrolysis | 88.1 | 89.1 | 87.6 |
| Inner Film | | | |
| Weight percent, based on total PVOH in blend | 70% | 30% | 100% |
| Anionic modification (mol %) | — | Maleate modified (4 mol %) | — |
| Viscosity (cP) | 13.4 | 16 | 14.1 |
| Degree of Hydrolysis | 86.9 | 89.1 | 87.6 |

Films and pouches were prepared according to Example 1. The outer film of Example 6, when formed into a single compartment pouch and tested according to the Pouch Strength Test, had a pouch strength of 560 N. The inner wall film of Example 6 had a Tackiness value of 1508 g/s as determined by the Tackiness PA test.

Thus, Example 6 demonstrates a two compartment pouch of the disclosure.

Example 7

Water soluble pouches having an inner film and outer films as described in Table 11, below, were prepared. The inner and outer films each further included about 38 phr plasticizers, about 6-7 phr surfactants, and minor amounts of processing aids e.g., filler, antifoam, bittering agents, antiblock, and bleaching agents in an amount totaling less than about 6-7 phr.

TABLE 11

|  | PVOH homopolymer | PVOH copolymer | Blend |
| --- | --- | --- | --- |
| Outer Film | | | |
| Weight percent, based on total PVOH in blend | 60% | 40% | 100% |
| Anionic modification (mol %) | — | Maleate modified (4 mol %) | — |
| Viscosity (cP) | 23.7 | 16 | 20.3 |
| Degree of Hydrolysis | 87.2 | 89.1 | 88.6 |
| Inner Film | | | |
| Weight percent, based on total PVOH in blend | 70% | 30% | 100% |
| Anionic modification (mol %) | — | Maleate modified (4 mol %) | — |
| Viscosity (cP) | 13.4 | 16 | 14.1 |
| Degree of Hydrolysis | 86.9 | 89.1 | 87.6 |

Films and pouches were prepared according to Example 1. The outer film of Example 7, when formed into a single compartment pouch and tested according to the Pouch Strength Test, had a pouch strength of 560 N. The inner wall film of Example 7 had a Tackiness value of 1508 g/s as determined by the Tackiness PA test.

Thus, Example 7 demonstrates a two compartment pouch of the disclosure.

Example 8

Water soluble pouches having an inner film and outer films as described in Table 12, below, were prepared. The inner and outer films each further included about 38 phr plasticizers, about 6-7 phr surfactants, and minor amounts of processing aids e.g., filler, antifoam, antiblock, and bleaching agents in an amount totaling less than about 6-7 phr.

TABLE 12

|  | PVOH homopolymer | PVOH copolymer | Blend |
| --- | --- | --- | --- |
| Outer Film | | | |
| Weight percent, based on total PVOH in blend | 60% | 40% | 100% |
| Anionic modification (mol %) | — | Maleate modified (4 mol %) | — |
| Viscosity (cP) | 21.8 | 16 | 19.3 |
| Degree of Hydrolysis | 87.4 | 89.1 | 88.1 |
| Inner Film | | | |
| Weight percent, based on total PVOH in blend | 70% | 30% | 100% |
| Anionic modification (mol %) | — | Maleate modified (4 mol %) | — |
| Viscosity (cP) | 12.5 | 16 | 13.5 |
| Degree of Hydrolysis | 85.9 | 89.1 | 86.9 |

Films and pouches were prepared according to Example 1. The outer film of Example 8, when formed into a single compartment pouch and tested according to the Pouch Strength Test, had a pouch strength of 355 N. The inner wall film of Example 8 had a Tackiness value of 2630 g/s as determined by the Tackiness PA test.

Thus, Example 8 demonstrates a two compartment pouch of the disclosure.

Example 9

Water-soluble pouches are made from films similar to those of Examples 1-8 above. The first film is made from a plasticized 60%/40% blend of homopolymer and 4% maleate copolymer, and the second film is made from a plasticized 70%/30% blend of homopolymer and 4% maleate copolymer. The films are sealed to each other using a sealing solution having water and plasticizer, without a surfactant. Initial pouch integrity is good. After storage, the seal strength between the films lessens.

Comparative water-soluble pouches are made from the same two films. The two films are sealed to each other using a sealing solution having water, plasticizer, and a surfactant. Initial pouch integrity is good. After storage, the seal strength between films improves, relative to the seal strength of the films sealed with a solution omitting the surfactant.

The foregoing description is given for clearness of understanding only, and no unnecessary limitations should be understood therefrom, as modifications within the scope of the invention may be apparent to those having ordinary skill in the art.

All patents, publications and references cited herein are hereby fully incorporated by reference. In case of conflict between the present disclosure and incorporated patents, publications and references, the present disclosure should control.

What is claimed:

1. A water soluble pouch defining an interior pouch volume, the pouch comprising at least two water-soluble films, wherein a first water soluble film of the at least two water-soluble films comprises a polyvinyl alcohol resin comprising a polyvinyl alcohol copolymer comprising an anionic monomer unit, optionally wherein the anionic monomer unit is derived from one or more of maleic acid, monoalkyl maleate, dialkyl maleate monomethyl maleate dimethyl maleate, maleic anhydride, alkali metal salts of the foregoing, and esters of the foregoing, and wherein the first water-soluble film comprising a polyvinyl alcohol copolymer comprising an anionic monomer unit is sealed to a second water-soluble film of the at least two water-soluble films using a sealing solution comprising water, one or more diols and/or glycols, and a surfactant.

2. The water-soluble pouch of claim 1, wherein the surfactant is one or more selected from polyoxyethylenated polyoxypropylene glycols, alcohol ethoxylates, alkylphenol ethoxylates, tertiary acetylenic glycols and alkanolamides (nonionics), polyoxyethylenated amines, quaternary ammonium salts and quaternized polyoxyethylenated amines (cationics), amine oxides, N-alkylbetaines and sulfobetaines (zwitterionics), dioctyl sodium sulfosuccinate, lactylated fatty acid esters of glycerin and propylene glycol, lactylic esters of fatty acids, sodium alkyl sulfates, polysorbate 20, polysorbate 60, polysorbate 65, polysorbate 80, lecithin, acetylated fatty acid esters of glycerin and propylene glycol, and acetylated esters of fatty acids.

3. The water-soluble pouch of claim 2, wherein the surfactant is one or more selected from polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, amine oxides, N-alkylbetaines, sulfobetaines, and combinations thereof.

4. The water-soluble pouch of claim 1, wherein the second water soluble film of the at least two water-soluble films comprises a polyvinyl alcohol resin comprising a polyvinyl alcohol copolymer comprising an anionic monomer unit, optionally wherein the anionic monomer unit is derived from one or more of maleic acid, monoalkyl maleate, dialkyl maleate monomethyl maleate dimethyl maleate, maleic anhydride, alkali metal salts of the foregoing, esters of the foregoing.

5. The pouch of claim 4, wherein one or both copolymer-containing polyvinyl alcohol resins have a 4% solution viscosity at 20° C. in a range of 12 cP to 25 cP.

6. The pouch of claim 5, wherein both the copolymer-containing polyvinyl alcohol resins have a 4% solution viscosity at 20° C. in a range of 14.5 cP to 25 cP.

7. The pouch of claim 4, wherein one or both of the films is a blend of the copolymer resin further comprising a polyvinyl alcohol homopolymer resin.

8. The pouch of claim 7, wherein the blend in one or both films comprises from 30 to 100 weight percent of the polyvinyl alcohol copolymer comprising an anionic monomer unit and from 0 to 70 weight percent of the polyvinyl alcohol homopolymer, based on the total weight of polyvinyl alcohol in the film.

9. The pouch of claim 4, wherein the anionic monomer unit in one or both films is selected from the group consisting of vinyl acetic acid, alkyl acrylates, maleic acid, monoalkyl maleate, dialkyl maleate, monomethyl maleate, dimethyl maleate, maleic anhydride, fumaric acid, monoalkyl fumarate, dialkyl fumarate, monomethyl fumarate, dimethyl fumarate, fumaric anhydride, itaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, mesaconic anhydride, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts of the foregoing, esters of the foregoing, and combinations of the foregoing.

10. The pouch of claim 9, wherein the anionic monomer unit in one or both films is derived from one or more of maleic acid, monoalkyl maleate, dialkyl maleate, monomethyl maleate, dimethyl maleate, maleic anhydride, alkali metal salts of the foregoing.

11. The pouch of claim 7, wherein the blend in one or both films comprises at least 65 weight percent of the polyvinyl alcohol copolymer comprising an anionic monomer based on the total weight of polyvinyl alcohol in the film.

12. The pouch of claim 4, wherein the polyvinyl alcohol copolymer in one or both films comprises from 2 to 8 mol % of the anionic monomer unit.

13. The pouch of claim 1, wherein the polyvinyl alcohol resin of the first water soluble film of the at least two water-soluble films has a degree of hydrolysis in a range of 87 to 93, or if a blend of polyvinyl alcohol resins is used then the arithmetic weight average degree of hydrolysis is in a range of 87 to 93.

14. The pouch of claim 4, wherein one or both anionic copolymer films is characterized by a pouch strength of less than 2000 N as measured by the film sealed, conditioned, and tested according to the Pouch Strength Test.

15. The pouch of claim 1, wherein the pouch has a pouch strength of at least 200 N as measured by the Pouch Strength Test.

16. The pouch of claim 4, wherein one or both copolymer-containing films further comprise a plasticizer.

17. The pouch of claim 16, wherein the plasticizer is selected from the group consisting of glycerin, trimethylol propane, sorbitol, and combinations thereof.

18. The pouch of claim 4, wherein one or both copolymer-containing films further comprise a surfactant.

19. The pouch of claim 18, wherein the surfactant is selected from the group consisting of polyoxyethylenated polyoxypropylene glycols, alcohol ethoxylates, alkylphenol ethoxylates, tertiary acetylenic glycols and alkanolamides, polyoxyethylenated amines, quaternary ammonium salts and quaternized polyoxyethylenated amines, and amine oxides, N-alkylbetaines, sulfobetaines, and combinations thereof.

20. The pouch of claim 1, wherein at least one film further comprises an aversive agent comprising a bitterant, a pungent, or a combination thereof.

21. The pouch of claim 4, wherein one or both copolymer-containing films has a tackiness value of at least 1500 g/s for the film tested according to the Tackiness PA Test.

22. A method of making a water-soluble pouch according to claim 1, comprising solvent sealing the first water-soluble film to the second water soluble film with a sealing solution comprising water, one or more diols and/or glycols, and a surfactant.

* * * * *